(12) United States Patent
Nabeshima

(10) Patent No.: US 8,197,424 B2
(45) Date of Patent: Jun. 12, 2012

(54) GUIDE WIRE

(75) Inventor: Yousuke Nabeshima, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 150 days.

(21) Appl. No.: 12/492,948

(22) Filed: Jun. 26, 2009

(65) Prior Publication Data

US 2010/0004561 A1 Jan. 7, 2010

Related U.S. Application Data

(60) Provisional application No. 61/078,096, filed on Jul. 3, 2008.

(30) Foreign Application Priority Data

Jun. 30, 2008 (JP) ................................. 2008-171827

(51) Int. Cl.
  *A61M 25/00* (2006.01)
(52) U.S. Cl. ........................................................ 600/585
(58) Field of Classification Search .................... 600/585
  See application file for complete search history.

(56) References Cited

U.S. PATENT DOCUMENTS

| | | | |
|---|---|---|---|
| 4,724,846 A * | 2/1988 | Evans, III ...................... | 600/585 |
| 5,095,915 A | 3/1992 | Engelson | |
| 5,147,317 A * | 9/1992 | Shank et al. ............. | 604/164.13 |
| 5,404,887 A | 4/1995 | Prather | |
| 5,437,288 A | 8/1995 | Schwartz et al. | |
| 5,507,995 A | 4/1996 | Schweich, Jr. et al. | |
| 5,746,701 A * | 5/1998 | Noone ........................... | 600/585 |
| 6,106,485 A * | 8/2000 | McMahon .................... | 600/585 |
| 6,251,085 B1 | 6/2001 | Tezuka | |
| 6,296,616 B1 | 10/2001 | McMahon | |
| 6,786,876 B2 * | 9/2004 | Cox ............................... | 600/585 |
| 2002/0087100 A1 | 7/2002 | Onuki et al. | |
| 2004/0167439 A1 | 8/2004 | Sharrow | |
| 2005/0096567 A1* | 5/2005 | Reynolds et al. ............. | 600/585 |
| 2005/0096665 A1 | 5/2005 | Reynolds et al. | |
| 2005/0148865 A1 | 7/2005 | Weber | |
| 2007/0255217 A1 | 11/2007 | Burkett et al. | |
| 2008/0119762 A1 | 5/2008 | Tateishi et al. | |
| 2008/0228109 A1 | 9/2008 | Kinoshita et al. | |

FOREIGN PATENT DOCUMENTS

| | | |
|---|---|---|
| JP | 62-231675 A | 10/1987 |
| JP | 05-168717 A | 7/1993 |
| JP | 7-328126 A | 12/1995 |
| JP | 10-118188 A | 5/1998 |
| WO | WO 2005/044358 A2 | 5/2005 |
| WO | WO 2008/126286 A1 | 10/2008 |
| WO | WO 2009/004876 A1 | 1/2009 |

OTHER PUBLICATIONS

Search Report issued Oct. 5, 2009 by the European Patent Office in corresponding European Application No. 09164038.3.

* cited by examiner

*Primary Examiner* — Max Hindenburg
*Assistant Examiner* — Charles Becker
(74) *Attorney, Agent, or Firm* — Buchanan Ingersoll & Rooney PC

(57) ABSTRACT

A guide wire is comprised of a flexible elongate wire body. The wire body has a plurality of protruding portions n the external surface and recessed portions between the adjacent protruding portions. The protruding portions possess a friction coefficient smaller than that of the recessed portions.

25 Claims, 12 Drawing Sheets

GUIDE WIRE

This application claims priority under 35 U.S.C. §119(e) to U.S. Provisional Application No. 61/078,096 filed on Jul. 3, 2008, the entire content of which is incorporated herein by reference. This application also claims priority under 35 U.S.C. §119(a) based on Japanese Application No. 2008-171827 filed on Jun. 30, 2008, the entire content of which is incorporated herein by reference.

TECHNOLOGICAL FIELD

The present invention relates generally to guide wires and more particularly to a guide wire used to introduce a catheter into a body cavity such as e.g. a blood vessel, a bile duct, etc.

BACKGROUND DISCUSSION

A guide wire is used to guide a catheter to treat or diagnose vascular stenosis in a cardiac artery or in a peripheral artery such as a limb or the like. The guide wire used for such procedure is inserted to the vicinity of a vascular stenosis site or a target site together with a catheter with the distal end of the guide wire allowed to project from the distal end of the catheter. In this state, the catheter is shifted along the guide wire to guide the distal end portion of the catheter to the vicinity of the vascular stenosis site.

The blood vessel requiring the above-mentioned procedure has an indurate stenosis site, a partially steeply bending flexion or the like. Therefore, the guide wire may be sometimes hard to pass through. Because of this, the guide wire used to guide the catheter into the blood vessel requires not only adequate flexibility and restoring performance for bending, but also pushability and torque transmissibility for transmitting the operation of the proximal end portion to the distal end side, and further anti-kink performance (anti-bending performance) and the like. (The pushability and torque transmissibility are generically referred to as "operability".)

To improve the operability (pushability) of the guide wire, the guide wire has been covered on an outer surface with a material adapted to make satisfactory the sliding performance with the catheter inner surface. An example is the guide wire described in Japanese Patent Laid-Open No. Hei 5-168717, referred to as Patent Document 1 hereinafter. The guide wire described in Patent Document 1 is such that a distal portion is coated with a hydrophilic resin and a proximal portion which is to be handled is covered with a fluorinated resin different from that for its distal end side portion in order to improve a grip force (gripping force) encountered when the guide wire is gripped at its hand portion. However, even if the portion to be handled is covered with the fluorinated resin, since the fluorinated resin surface has a relatively low friction coefficient relative to a finger, the grip force is not increased. That is to say, there arises a problem in that since the portion to be handled is slippery, a pushing and turning force is hard to transmit depending upon a to-be-inserted site or a catheter so that operability is not high.

There is a guide wire that is covered with a hydrophilic resin, wherein the distal end side portion of its covering layer is removed and a spiral slip-prevention member is provided at such a removed portion. An example is disclosed in Japanese Patent Laid-Open No. Hei 7-328126, referred to as Patent Document 2 hereinafter. However, although the guide wire described in Patent Document 2 exhibits a grip force when operated by gripping the portion provided with the slip-prevention member, if such a portion is inserted into the lumen of the catheter, just then the slip-prevention member functions to lower sliding performance. If the slip-prevention member is provided only at the proximal end of the guide wire, the intermediate portion of the guide wire, i.e., a portion not provided with the slip-prevention member will be gripped during insertion. Therefore, the hydrophilic resin (the covering layer) functions to lower the grip force, so that unnecessary time will be spent for the insertion.

There is also a guide wire in which a wire is spirally wound to form concavity and convexity on a jacket surface (a covering layer) made of PTFE or the like and thereafter the convexity is subjected to hydrophilic or hydrophobic coating. An example is disclosed in International Application Publication No. WO 05/44358 referred to as Patent Document 3 hereinafter. Although the guide wire described in Patent Document 3 improves sliding performance, since the material with a low friction coefficient such as PTFE or the like is used as the material forming the jacket, an improvement in grip force cannot be expected. Further, the step for forming concavity and convexity is complicated and it is difficult to form uniform concavity and convexity.

SUMMARY

A guide wire disclosed here is comprised of a flexible elongate wire body. The wire body has a protruding portion formed on the external surface of the wire body, and non-protruding portion between the adjacent protruding portion. The protruding portion is formed of a material having a friction coefficient smaller than that of a material forming the non-protruding portion.

The top of the protruding portion is preferably formed of a fluorinated resin material.

Also, it is preferable that the top of the protruding portion is rounded.

The bottom of the non-protruding portion has a portion extending linearly along a longitudinal direction of the wire body as viewed in longitudinal cross-section.

According to another aspect, a guide wire including a flexible elongate wire body, wherein the wire body has a protruding portion on its external surface and the non-protruding portion located between the adjacent protruding portion. During use of the guide wire, sliding resistance encountered when a top of the protruding portion comes into main contact is smaller than that encountered when also a bottom of the non-protruding portion comes into contact, so that the top is more slippery than the bottom.

In the guide wire disclosed here, it is preferred that an occupancy of the protruding portion on the external surface be smaller than that of the non-protruding portions. Also, it is preferred that the bottom of the non-protruding portion be roughened.

In the guide wire disclosed here, the protruding portion is preferably formed of at least one linear member, and can be configured in a spiral or ring-shaped manner.

The protruding portion can be formed of two spirally extending linear members whose spiral winding directions are opposite to each other.

According to other possibilities, the linear member can be formed to linearly extend along the longitudinal direction of the wire body.

Also, in the guide wire disclosed here, the protruding portion can be composed of a plurality of the linear members, with the linear members arranged at given intervals along a circumferential direction of the external surface.

According to another variation, the protruding portion can be arranged in a scattered manner.

In the guide wire disclosed here, it is preferred that the protruding portion has a high-density part and a low-density part located closer to the proximal end side than the high-density part, with the high-density part and the low-density part being different in arrangement density from each other.

The wire body preferably has a tapered section gradually reduced in outer diameter toward the distal end and an outer diameter-uniform section provided at a proximal end of the taper section and having an uniform outer diameter.

In the guide wire disclosed here, it is preferred that the high-density part is spanned from the tapered section to the outer diameter-uniform section. It is also preferable that the low-density part be located at the outer diameter-uniform section.

In the guide wire disclosed here, the protruding portion can be formed by applying a liquid material to the wire body and then drying it.

According to the disclosure here, when the guide wire is inserted into the tube-cavity such as, for example, the lumen of a catheter or the like, a portion located (inserted) in the tube-cavity of the guide wire is such that the respective protruding portion low in friction coefficient come into main contact with the inner wall partitioning the tube-cavity but the non-protruding portion high in friction coefficient is prevented from coming into contact with the inner wall. Thus, when the guide wire is operatively shifted along the axial direction or turned around its axis, the protruding portion will be slid along the inner wall, which exhibits satisfactory sliding performance.

At a gripped portion of the guide wire, for example, a finger is able to enter (be positioned in) the non-protruding portion. The front surface of the finger comes into contact with the bottom of the non-protruding portion high in friction coefficient rather than comes into abutment against the respective protruding portion low in friction coefficient. Thus, the grip force (the gripping force) can reliably be prevented from lowering when the guide wire is operatively shifted or turned, so that the operating force (the pushability, torque) at that time is reliably transmitted to the distal end of the guide wire. It is an object disclosed here to provide a guide wire that can reliably prevent a grip force (gripping force) from lowering when the guide wire is operatively gripped while exhibiting satisfactory sliding performance within a tube-cavity such as a lumen of a catheter or the like.

According to another aspect, a guide comprises an elongated flexible wire body comprising a distal end portion and a proximal end portion, a first constant diameter section at which the outer diameter of the elongated flexible wire body is a constant outer diameter, a second constant diameter section at which the outer diameter of the elongated flexible wire body is a constant outer diameter less than the constant outer diameter of the first constant diameter section, and a tapered section at which the outer diameter of the elongated flexible wire body varies from the constant outer diameter of the first constant diameter section to the constant outer diameter of the second constant diameter section. The tapered section is positioned axially between the first constant diameter section and the second constant diameter section, and the first constant diameter section is positioned distally of the second constant diameter section. The wire body also comprises a plurality of radially outward protruding portions spaced apart from one another. The protruding portions extend further radially outwardly than portions of the outer surface of the flexible wire body surrounding the protruding portions so that recessed portions exist between adjacent protruding portions. The guide wire thus possesses an undulating outermost surface by virtue of the protruding portions and the recessed portions. The protruding portions are located in the first constant diameter section, the tapered section, and the second constant diameter section, and the protruding portions have an outer surface made of a material possessing a friction coefficient smaller than the friction coefficient of material forming the outer surface of the flexible wire body in the recessed portions.

DETAILED DESCRIPTION

FIGS. 1-4 illustrate one embodiment of a guide wire disclosed here. FIG. 11 is a graph showing respective friction coefficients of a protruding portion and a recessed portion of the guide wire embodiment illustrated in FIGS. 1-4. In FIGS. 1-4, the right and left are referred to as "the proximal end" and "the distal end," respectively. This also applies to the other embodiments illustrated in FIGS. 5-10 and described in more detail below. In addition, to facilitate an understanding, FIGS. 1 to 10 illustrate the guide wire shortened in the longitudinal length and exaggerated in diameter. Thus, the ratio between the longitudinal length and the diameter as illustrated is different from the actual ratio.

Figure 1:
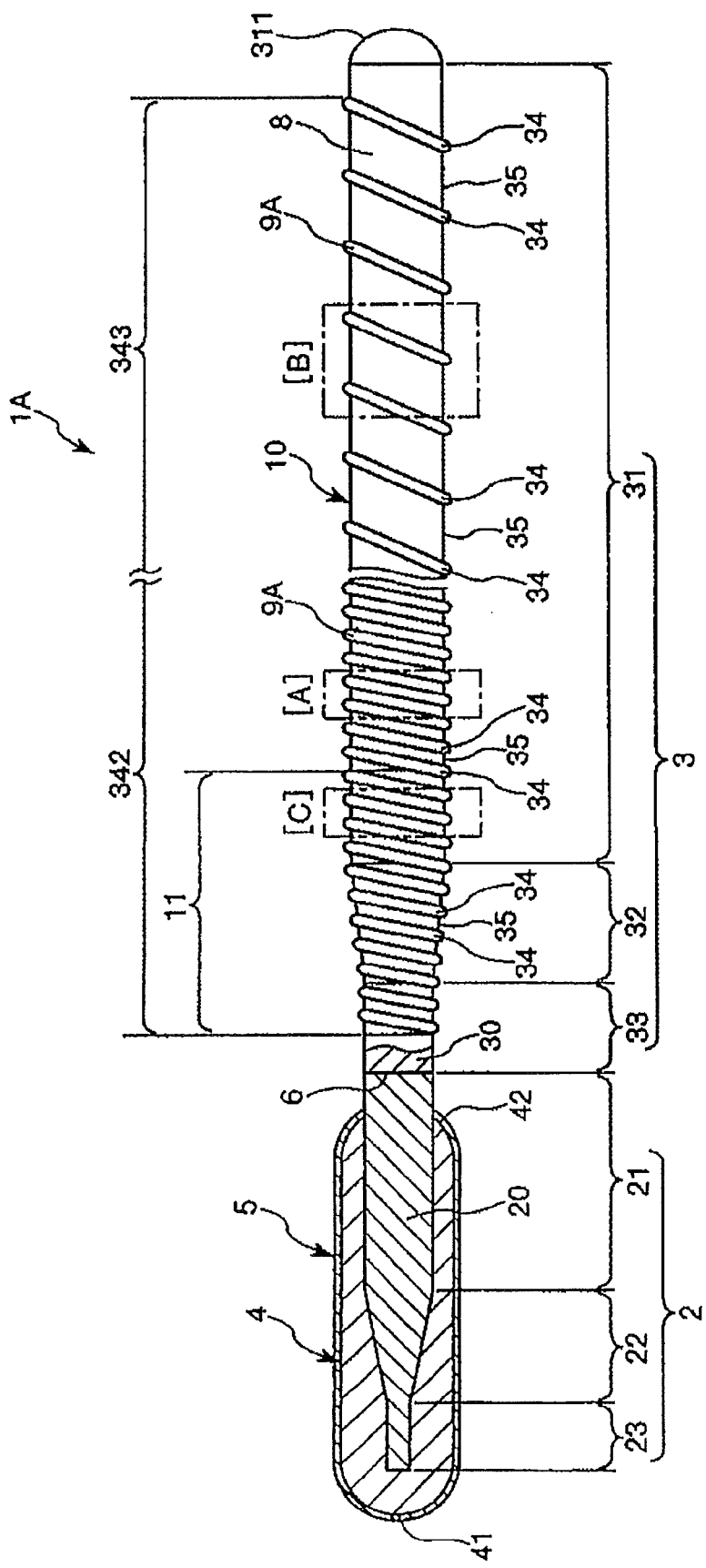
FIG. 1 is a partial longitudinal cross-sectional view illustrating a first embodiment of a guide wire disclosed here.

The guide wire 1A illustrated in FIG. 1 is a guide wire for catheter inserted into an inner cavity (lumen) 201 of a catheter 200 (including an endoscope) during use. The guide wire 1A includes an elongate wire body 10 and a distal end member 4. The wire body 10 is composed of a first wire 2 disposed on the distal end side and a second wire 3 disposed on the proximal end side of the first wire 2. The first wire 2 and the second wire 3 are joined together (connected to each other) preferably by welding. Although not particularly restrictive, the overall length of the guide wire 1A is preferably about 200 to 5000 mm.

The first wire 2 is made of a flexible or elastic core (wire rod) 20. Although not restrictive, the length of the first wire 2 is preferably about 20 to 1000 mm.

In the present embodiment, the first wire 2 includes: a large diameter section 21 with a substantially uniform outer diameter constituting a constant diameter section; a small diameter section 23, constituting another constant diameter section, located closer to the distal end than the large diameter section 21 and having an outer diameter smaller than that of the large diameter section 21; and a tapered section 22 located between the large diameter section 21 and the small diameter section 23 so as to gradually decrease in outer diameter in the distal end direction. The sections are arranged in the order of the small diameter section 23, the tapered section 22 and the large diameter section 21 from the distal end side of the first wire 2 toward the proximal end side.

The small diameter section 23 and the large diameter section 21 are formed via the tapered section 22 and so the first wire 2 can gradually be reduced in rigidity (bending rigidity, torsional rigidity) toward the distal end. Consequently, the guide wire 1A can have satisfactory flexibility and narrowed-area passability at its distal end portion so as to improve following performance and safety with respect to a blood vessel, etc., and help prevent bending and the like.

The taper angle (the reduction ratio of the outer diameter) of the tapered section 22 may be constant along the wire-longitudinal direction or may partially vary in the longitudinal direction. For example, the tapered section 22 may be formed such that a portion having a relatively large taper angle (the reduction ratio of the outer diameter) and a portion having a relatively small taper angle are alternately repeated a plurality of times.

The proximal end side portion of the first wire, i.e., the large diameter portion 21, is constant up to the proximal end of the first wire 2.

The distal end (distal end face) of the second wire 3 is joined (connected) to the proximal end (proximal end face) of the first wire 2 (the distal end of the large diameter section 21) preferably by welding. The second wire 3 has a flexible or elastic core (wire rod) 30.

Although not limited in this regard, examples of a welding method between the first wire 2 (the core 20) and the second wire 3 (the core 30) include friction pressure welding, laser spot welding, and butt resistance welding such as butt seam welding. Because it provides relative simplicity and high-joint strength, the butt resistance welding is particularly preferable.

In the present embodiment, the second wire 3 includes: a large diameter section (an outer diameter uniform section) 31 having a substantially uniform outer diameter; a small diameter section 33 located closer to the distal end than the large diameter section 31 and having an outer diameter smaller than that of the large diameter section 31; and a tapered section 32 between the large diameter section 31 and the small diameter section 33, and possessing a gradually reduced outer diameter toward the distal end. These sections of the second wire 3 are arranged in the order of the small diameter section 33, the tapered section 32 and the large diameter section 31 from the distal end side of the second wire 3 toward the proximal end side. The outer diameter of the distal end portion of the small diameter section 33 is substantially equal to that of the large diameter section 21 of the first wire 2. Thus, when the proximal end (proximal end face) of the large diameter section 21 of the first wire 2 is joined to the distal end of the small diameter section 33 of the second wire 3, a step due to differences in outer diameter between the wires 2, 3 will not occur on the outer circumference of the joint portion (the joint surface) 6. Thus, a continuous smooth surface exists at the joint.

The second wire 3 is such that the small diameter section 33 and the large diameter section 31 are formed via the tapered section 32. Therefore, the second wire 3 can gradually be reduced in rigidity (bending rigidity, torsional rigidity) toward the distal end. Consequently, the guide wire 1A can have satisfactory flexibility at the second wire 3, similar to the first wire 2, so as to improve following performance and safety with respect to a blood vessel, etc., and prevent bending and the like. Further, since physical characteristics, especially, elasticity smoothly varies from the second wire 3 to the first wire 2, even the front and rear of the joint portion (joint surface) 6 of both the wires 2, 3 can exhibit satisfactory pushability and torque transmissibility, thereby improving anti-kink performance.

The large diameter section 31 of the second wire 3 has an outer diameter greater than the outer diameter (the maximum outer diameter of the first wire 2) of the large diameter section 21 of the first wire 2. The outer diameter of the large diameter section 31 may be e.g. 1.02 to 5 times that of the large diameter section 21. In addition, the proximal end 311 of the large diameter section 31 is rounded.

The taper angle (the reduction ratio of the outer diameter) of the tapered section 32 may be constant along the wire-longitudinal direction or may partially change in the longitudinal direction. For example, the tapered section 32 may be formed such that a portion having a relatively large taper angle (the reduction ratio of the outer diameter) and a portion having a relatively small taper angle are alternately repeated a plurality of times. A plurality of such taper sections may be provided along the wire-longitudinal direction.

Although not particularly restrictive, the length of the second wire 3 is preferably about 20 to 4800 mm, more preferably about 1400 to 3000 mm.

The average outer diameter of the first wire 2 is smaller than that of the second wire 3. Therefore, the guide wire 1A is such that the first wire 2, i.e., its distal end side, is relatively quite flexible and the second wire 3, i.e., its proximal end side, is relatively highly rigid. Thus, the flexibility of the distal end portion and excellent operability (pushability, torque transmissibility, etc.) can be combined together.

The constituent material of the wire rod 20 of the first wire 2 and of the wire rod 30 of the second wire 3 is not particularly restrictive as long as it is flexible. Examples of the constituent material include various metal materials such as stainless steel (e.g., SUS304, SUS303, SUS316, SUS316L, SUS316J1, SUS316J1L, SUS405, SUS430, SUS434, SUS444, SUS429, SUS430F, SUS302, and the other SUS materials), a piano wire, a cobalt-based alloy, and a pseudoelastic alloy (including a superelastic alloy). Among them, the pseudoelastic alloy (including a superelastic alloy) is particularly preferred, and the superelastic material is more preferred.

A superelastic alloy is relatively flexible, has restoring performance and is less prone to have bending tendency. Therefore, for example, if the first wire 2 is made of a superelastic alloy, the guide wire 1A has sufficient flexibility and restoring performance for bending at its distal end portion. Thus, a capability of following a complicatedly curving and bending blood vessel or the like is improved to provide more excellent operability. In addition, even if the first wire 2 is repeatedly subjected to curving and bending deformation, it does not exhibit bending tendency because of the inherent restoring performance of the first wire 2. Thus, it is possible to prevent the deterioration of operability resulting otherwise from the first wire 2 being subjected to bending tendency during the use of the guide wire 1A.

A cobalt-based alloy formed into a wire has a high degree of elasticity and an appropriate elastic limit. Thus, the wire made of a cobalt-based alloy has excellent torque transmissibility and rarely causes a problem such as buckling or the like. Any cobalt-based alloy may be used as long as it contains Co as a constituent element. However, a cobalt-based alloy containing Co as a chief ingredient (Co-based alloy: alloy having a highest rate of content of Co in weight-ratio among elements constituting the alloy) is preferable. A Co—Ni—Cr-based alloy may more preferably be used. Use of the alloys having such compositions makes the effect described above further remarkable. The alloys having such compositions have a high-elastic coefficient and can be cold-formed, though having a high elastic limit. Having the high elastic limit, the alloy having such compositions can reduce its diameter while sufficiently preventing the occurrence of buckling. Consequently, it can have flexibility and rigidity sufficient to be inserted into a desired site.

Examples of a CO—Ni—Cr-based alloy include an alloy having a composition of 28 to 50 wt % Co-10 to 30 wt % Ni-10 to 30 wt % Cr-remnant Fe; and an alloy whose part is substituted by another element (substitution element). Inclusion of a substitution element exhibits an inherent effect depending on its type. For example, the strength of the second wire 3 can be further increased by containing at least one selected from the group consisting of e.g. Ti, Nb, Ta, Be and Mo as a substitution element. Incidentally, if an element other than Co, Ni and Cr is contained, it is preferred that its content (of the overall substitution element) be 30 wt % or less.

A part of Co, Ni and Cr may be substituted by another element. For example, Mn can be substituted for a part of Ni. This can further improve workability. Mo and/or W can be substituted for a part of Cr. This can further improve an elastic limit. Among Co—Ni—Cr-based alloys, a Co—Ni—Cr—Mo-based alloy containing Mo is particularly preferable.

The core 20 of the first wire 2 and the core 30 of the second wire 3 may be composed of respective different materials. However, in the present embodiment, they are made of the identical metal material or of the same type metal material (the phrase "same type metal material" means that the cores are made of alloys in which the material constituting the largest percentage content in each is the same). This can increase the joint strength of the joint portion (welded portion) 6. Thus, although the outer diameter of the joint portion 6 is small, separation or the like will not occur and so superior torque transmissibility is exhibited.

In this case, each of the first wire 2 (the core 20) and the second wire 3 (the core 30) may preferably be made of the superelastic alloys described above, more preferably a Ni—Ti-based alloy among them. Thus, the wire body 10 can ensure superior flexibility on the distal end side from the joint portion 6 and sufficient rigidity (bending rigidity, torsional rigidity) on the proximal end side portion of the wire body 10. Consequently, while providing superior pushability and torsional transmissibility to ensure satisfactory operability, the guide wire 1A provides satisfactory flexibility and restoring performance on the distal end side to improve a following capability and safety for a blood vessel, a bile duct and a pancreatic duct.

The first wire 2 and the second wire 3 may be made of different materials. In such a case, the first wire 2 is preferably made of a superelastic alloy, more preferably a Ni—Ti-based alloy. In addition, the second wire 3 is preferably made of the stainless steel described above.

Alternatively, the first wire 2 and the second wire 3 may be made of pseudoelastic alloys or stainless steel alloys different from each other in metal composition and in physical characteristic.

The above-description describes a construction in which the first wire 2 and the second wire 3 are joined together. However, a wire made of a single member without the joint portion may be applicable. In such a case, examples of the constituent material of the wire include the same materials as described earlier, particularly preferably stainless steel, a cobalt-based alloy and a pseudoelastic alloy.

As illustrated in FIG. 1, a distal end member 4 is disposed on the outer circumference of the distal end portion of the wire body 10. The distal end member 4 covers a portion of the first wire 2 from the distal end of the first wire 2 to the middle portion or intermediate region of the large diameter section 21. In the illustrated embodiment, the distal end member 4 covers less than the entire length of the first wire member. The installation or application of the distal end member 4 reduces the contact area of the external surface of the wire body 10 with the inner wall 202 of the catheter 200 or with a living body surface. This can reduce sliding resistance, with the result that the operability of the guide wire 1A is improved.

The distal end member 4 is configured as a circular cylinder possessing a constant outer diameter in the longitudinal direction of the wire body 10. The distal end member 4 has a distal end 41 and a proximal end 42 which are both rounded. By virtue of the rounded distal end 41 of the distal end member 4, when the guide wire 1A is inserted into a body cavity such as a blood vessel, damage to its inner wall can more effectively be prevented to enhance safety.

The distal end member 4 is preferably made of a flexible material (a soft material, an elastic material). Examples of such a flexible material include polyolefin such as polyethylene and polypropylene, polyvinyl chloride, polyester (PET, PBT, etc.), polyamide, polyimide, polyurethane, polystyrene, a silicone resin, thermoplastic elastomer such as polyurethane elastomer, polyester elastomer and polyamide elastomer, rubber materials such as latex rubber and silicon rubber, and a complex material combining two or more among them. In particular if the distal end member 4 is made of the thermoplastic elastomer or various rubber materials described above, the flexibility of the distal end portion of the guide wire 1A is more improved. Therefore, when the guide wire 1A is inserted into a blood vessel or the like, a blood vessel inner wall or the like can reliably be prevented from being damaged to provide an extremely high degree of safety. In addition, such resin materials are superior in adhesion to a superelastic alloy represented by the Ni—Ti alloy mentioned above. Thus, the distal end member 4 is reliably secured to the first wire 2. In the illustrated embodiment, the distal end member 4 is in direct contact with the first wire member 2 (i.e., the inner surface of the distal end member 4 directly contacts the outer surface of the first wire member 2).

Although not particularly limited in this regard, the length of the distal end member 4 is preferably about 5 to 700 mm, more preferably about 50 to 500 mm.

Fillers (particles) made of a material with contrast performance (radiopaque material, etc.) may be scattered in the distal end member 4 to form a contrast portion.

As illustrated in FIG. 1, the external surface of the distal end member 4 is covered by a covering layer 5. This covering layer 5 is formed by coating the outer surface of the distal end member 4 with a hydrophilic material. The hydrophilic material becomes wet to cause lubricating ability, which reduces the friction (friction resistance) of the guide wire 1A to improve sliding performance. Thus, the operability of the guide wire 1A is improved.

Examples of the hydrophilic material include: a cellulosic high-molecular material, polyethylene oxide high-molecular material, maleic acid anhydride high-molecular substance (e.g. maleicacid anhydride copolymer such as methylvinylether-maleicacidanhydride), acrylamide-based high-molecular material (e.g. polyacrylamide, block copolymer of polyglycidylmethacrylate-dimethylacrylamide (PGMA-DMAA), water-soluble nylon, polyvinyl alcohol, and polyvinylpyrrolidone.

Such hydrophilic materials exhibit lubricating ability resulting from moistness (water absorption) in many cases to reduce the frictional resistance (sliding resistance) with the inner wall 202 of the catheter 200 used together with the guide wire 1A. Thus, the sliding performance of the guide wire 1A can be improved to provide more satisfactory operability of the guide wire 1A in the catheter 200.

Figure 2:
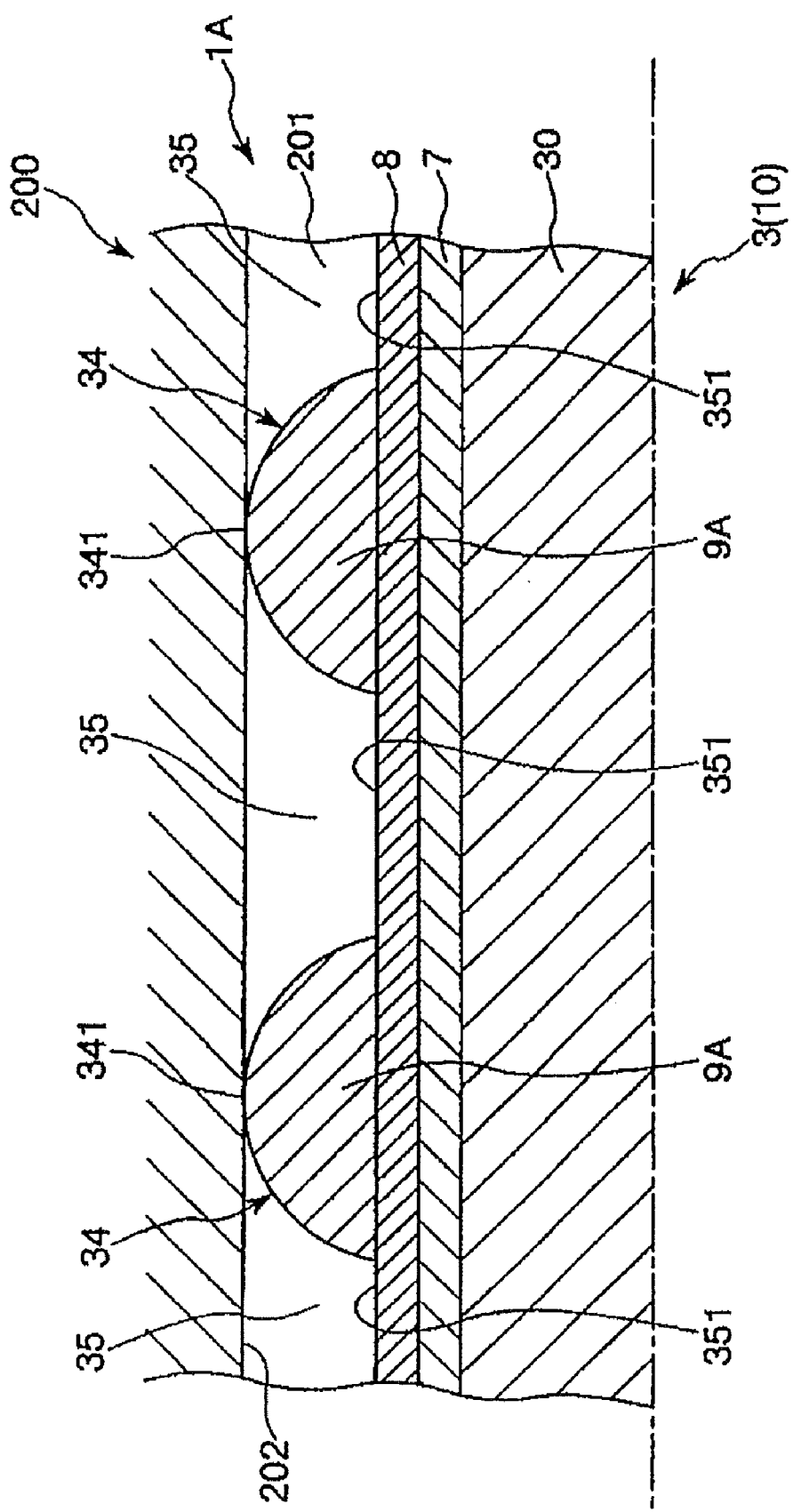
FIG. 2 is an enlarged longitudinal cross-sectional view of the area [A] surrounded by a chain line in FIG. 1.
Figure 3:
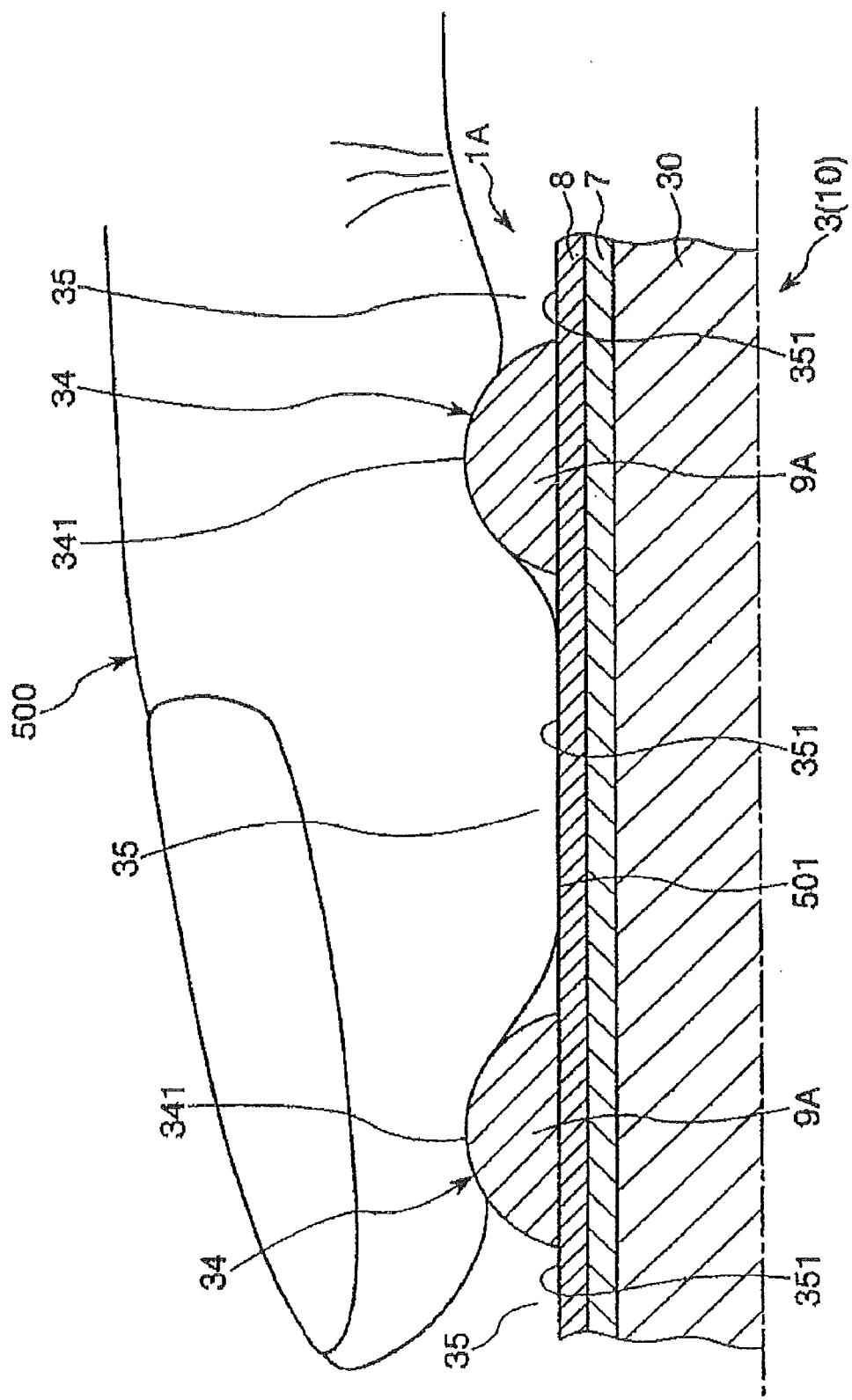
FIG. 3 is an enlarged longitudinal cross-sectional view of the area [B] surrounded by a chain line in FIG. 1.

FIGS. 2 and 3 illustrate that the second wire 3 is comprised of an inner layer 7, an outer layer 8 and a linear member (a first linear portion) 9A formed (laminated) in this order on the outer circumferential side of the core 30.

The inner layer 7 is applied directly on the outer circumference of the core 30. The inner layer 7 is formed of a material containing resin and pigment.

Although not particularly restrictive, examples of the resin material in the inner layer 7 preferably include a fluorinated resin material. The inner layer 7 contains two kinds of fluorinated resin materials different in composition from each other. The two kinds of resin materials can be such that, for example, one is polytetrafluoroethylene (PTFE) and the other is fluorinated ethylene propylene (FEP).

Although the pigment in the inner layer 7 may be any of inorganic pigment and organic pigment, inorganic pigment is preferable in view of thermal resistance during the formation of the inner layer 7. Usable examples of the inorganic pigment include carbon black, isinglass, titanium dioxide, nickel titanium yellow, Prussian blue, Milori blue, cobalt blue, ultramarine, and Viridian. One kind of pigment may be used alone, but two or more may be used together (specially mixed). Although not particularly restrictive, the average diameter of the pigment is preferably e.g. 0.3 to 5 μm, more preferably 0.5 to 3 μm. Depending on the kind and characteristic of pigment and on the composition of the resin material, the content of the pigment in the inner layer 7 is preferably about 20 to 50 wt %, more preferably about 30 to 40 wt % relative to the overall inner layer 7.

Since the inner layer 7 is formed on the outer circumference of the core 30, the constituent materials of the inner layer 7 include a resin material functioning as a binder to improve adhesion with the core 30, for example. Although not particularly restrictive, examples of the resin material include polysulphone, polyimide, polyether ether ketone, polyarylene ketone, polyphenylene sulfide, polyarylene sulfide, polyamideimide, polyetherimide, polyimide sulfone, polyaryl sulfone, polyaryl ether sulfone, polyester, and polyethersulfone.

Though not limited in this regard, the thickness of the inner layer 7 is preferably e.g. 0.002 to 0.015 mm, more preferably 0.004 to 0.008 mm.

The outer layer 8 is formed on the inner layer 7. In the illustrated embodiment, the outer layer 8 is formed directly on the inner layer 7 so that the inner surface of the outer layer directly contacts the outer surface of the inner layer 7. The outer layer 8 is preferably formed of a material containing e.g. resin and pigment.

As an example, a fluorinated resin material is preferably used as the resin in the outer layer 8, similar to the inner layer 7. For example, polytetrafluoroethylene (PTFE), fluorinated ethylene propylene (FEP) or the like can be used as the fluorinated resin material.

The pigment in the outer layer 8 may be any of inorganic pigment and organic pigment. The inorganic pigment is preferred in view of thermal resistance during formation of the outer layer 8. The same materials as those included in the description of the inner layer 7 can be used as the inorganic material. Depending on the kind and characteristic of the pigment and on the composition and characteristic of a resin material, for example, the content of the pigment of the outer layer 8 is preferably about 10 to 50 wt %, more preferably 20 to 30 wt %, of the overall outer layer 8.

Though not particularly restrictive, the thickness of the outer layer 8 is preferably 0.002 to 0.015 mm, more preferably, 0.005 to 0.010 mm.

The linear member 9A is provided or formed on the outer layer 8. The linear member 9A is spirally wounded around the outer layer 8 as shown in FIG. 1. In this way, the linear member 9A is provided over the overall circumference of the second wire 3, meaning the linear member 9A extends from the distal end of the second wire member 3 to the proximal end of the second wire member 3. In addition, the linear member 9A is non-densely wound such that adjacent linear members are separate from each other. That is, axially adjacent windings of the linear member are axially spaced apart from one another. In the present embodiment, the linear member can be comprised of a single linear member as is the case with the illustrated embodiment or can be comprised of plural linear member portions. If the linear member is comprised of a number of linear member portions 9A, the spirally wound direction of the respective linear member portions is the same.

The linear members 9A results in the outer surface of the second wire 3 (the wire body 10) being provided with a plurality of radially outwardly protruding portions 34 composed of the linear members 9A and recessed portions 35 (i.e., non-protruding portions) each defined between axially adjacent protruding portions 34 (the linear members 9A). The plurality of protruding portions 34 are axially spaced apart from one another. In addition, the protruding portions 34 extend further radially outwardly than the recessed portions 35, meaning that the protruding portions 34 are elevationally above or higher than the recessed portions 35.

The linear member 9A is preferably made of a material containing resin and pigment.

Though not limited in this regard, a fluorinated resin material is an example of a material preferably used as the resin material in the linear member 9A, similar to the inner layer 7. For example, polytetrafluoroethylene (PTFE), fluorinated ethylene propylene (FEP) or the like can be used as the fluorinated resin material.

The pigment in the linear member 9A may be any inorganic pigment or organic pigment. The inorganic pigment is preferred in view of thermal resistance during formation of the linear member 9A. The same materials as those included in the description of the inner layer 7 can be used as the inorganic material here. Depending on the kind and characteristic of the pigment, and the composition and characteristic of the resin material, the content of the pigment of the linear member 9A is preferably about 1 to 8 wt %, more preferably about 3 to 5 wt %, of the overall linear member 9A.

In the guide wire 1A, the friction coefficient of the linear member 9A (the protruding portion 34) is smaller than that of the bottom 351 (an exposed portion of the outer layer 8) of the recessed portion 35. To achieve this difference/relationship in the friction coefficients, the following constituents can be included for example.

[1] Employing an arrangement in which the linear member 9A is made of PTFE and the outer layer 8 is made of FEP PTFE is a material having a friction coefficient smaller than that of FEP. Thus, with the linear member 9A made of PTFE and the outer layer 8 made of FEP, the friction coefficient of the protruding portion 34 is smaller than that of the bottom 351 of the recessed portion 35.

[2] Employing a construction in which the linear member 9A is made of PTFE and the outer layer 8 is made of a material containing PTFE and pigment (or a binder resin)

If pigment or a binder resin, which is a material having a friction coefficient larger (i.e., greater) than that of PTFE, is blended with PTFE, the friction coefficient of the overall material composition is greater than that of a material made of PTFE alone. Because of this, also if the linear member 9A is made of PTFE and the outer layer 8 is made of a material containing PTFE and pigment and/or a binder resin, the friction coefficient of the protruding portion 34 is less than that of the bottom 351 of the recessed portion 35.

[3] Employing a construction in which the linear member 9A and the outer layer 8 are made of the same resin material, but a content rate (contained amount) of pigment in one of the resin material compositions is different from that in the other If the content rate of the pigment in the linear member 9A is smaller than that in the outer layer 8, the friction coefficient of the protruding portion 34 is smaller than that of the bottom 351 of the recessed portion 35.

With constructions such as those discussed above the friction coefficient of the protruding portion 34 is reliably smaller than that of the bottom 351 of the recessed portion 35. Thus, the top 341 of the protruding portion 34 becomes more abhesive (more slippery) than the bottom 351 of the recessed portion 35.

The guide wire 1A configured as discussed above is used, for example, by being inserted into the lumen 201 of the catheter 200. This state is hereinafter called "the inserted state" and an example of this state is shown in FIG. 2. In this inserted state, while a portion of the guide wire 1A projects or is exposed outside the lumen, the proximal end of the catheter 200 of the guide wire 1A is gripped, the guide wire 1A is shifted along its axial direction or turned around its axis. In this way, the guide wire 1A can be operated.

As illustrated in FIG. 2, a portion of the guide wire 1A that is inserted into the lumen 201 of the catheter 200 is discussed below. The top 341 of each protruding portion 34 (the linear member 9A) and portions of the linear member 9A adjacent the top each having a relatively low friction coefficient come into abutment against (contact with) the inner wall 202 of the catheter 200. In addition, the bottom 351 of each recessed portion 35 having a relatively high friction coefficient are prevented from coming into abutment against the inner wall 202 of the catheter 200. Thus, when the guide wire 1A is operated, the tops 341 of the protruding portions 34 slide along the inner wall 202 of the catheter 200, exhibiting satisfactory sliding performance.

Also, referring to FIG. 3, at a hand engaging portion (a grip portion), a fingertip 500 (finger) is inserted into the recessed portion 35. Specifically, the skin (surface) 501 of the fingertip 500 mainly comes into abutment against (contact with) the bottom 351 of the recessed portion 35 having a relatively high friction coefficient rather than coming into abutment against each protruding portion 34 having a relatively low friction coefficient. Thus, when the guide wire 1A is operated, the fingertip 500 can reliably be prevented from slipping against the guide wire 1A. That is, a grip force (gripping force) can reliably be prevented from being lowered. Consequently, the pushability and torque at the hand portion can be reliably transmitted to the distal end of the guide wire 1A.

As described above, the guide wire 1A is formed with the portions whose external surface exhibit or possess different friction coefficient from each other. Therefore, there are portions different in sliding resistance from each other depending on the counterpart abutted in the used state. That is to say, there occurs a portion having a smaller sliding resistance encountered when it comes into main contact with the top 341 of the protruding portion 34 than that encountered when it comes into contact with the bottom 351 of the recessed portion 35.

FIG. 11 illustrates, by way of example, respective friction coefficients of the protruding portion 34 and the recessed portion 35. A testing method (measuring method) for determining the respective friction coefficients is discussed below.

This test used a Nanotribometer (manufactured by Nanotec Corporation) as the test equipment (measuring equipment). In this test equipment, a measuring terminal that is adapted to come into abutment against the protruding portion 34 and recessed portion 35 of the guide wire 1A is a terminal made of ruby having an outer diameter of 1.5 mm. The measuring terminal was pressed against the protruding portion 34 (or the recessed portion 35) at a pressing force of 50 mN, and was then shifted or moved by 0.1 mm at a sliding rate of 0.50 mm/sec. Such shifting or movement was repeated 50 times (reciprocated 50 times). The average value of such friction coefficients was obtained and the average value thus obtained was defined as a friction coefficient of the protruding portion 34 (or the recessed portion 35). In FIG. 11, the friction coefficient of the protruding portion 34 is 0.024 and the friction coefficient of the recessed portion 35 is 0.048.

Figure 4:
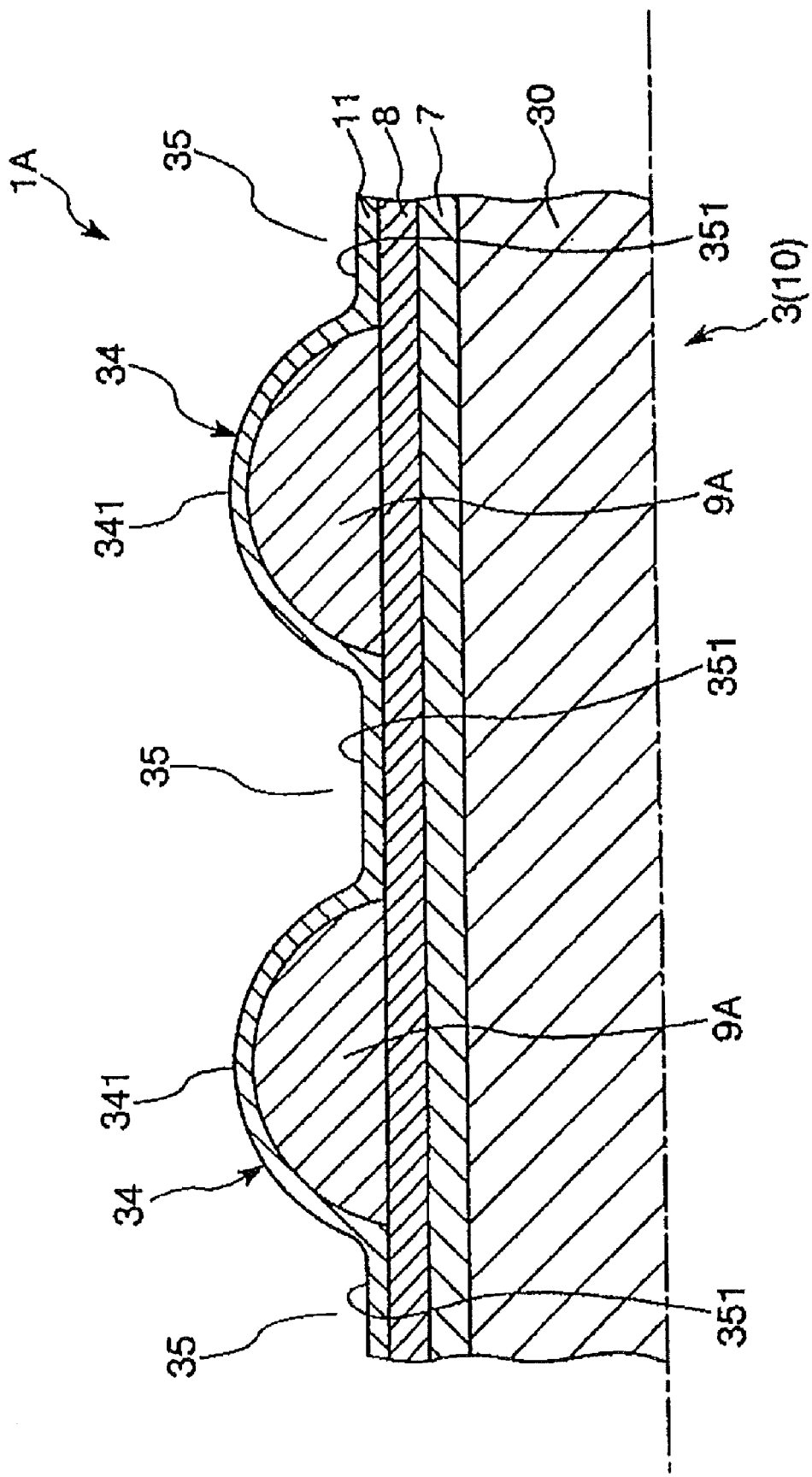
FIG. 4 is an enlarged longitudinal cross-sectional view of the area [C] surrounded by a chain line in FIG. 1.

As illustrated in FIGS. 2-4, the protruding portions 34 are each semi-circular in shape (taken along a longitudinal cross-section of the guide wire or a transverse cross-section of just the linear member) so that they are convexly curved, possessing a rounded top 341. In the inserted state, this reduces a contact area between the top 341 of the protruding portion 34 and the inner wall 202 of the catheter 200 to reduce the friction resistance (sliding resistance), which improves sliding performance, thereby make the operability of the guide wire 1A satisfactory.

The bottom 351 of the recessed portion 35 is formed linearly along the longitudinal direction of the wire body 10 in a longitudinal cross-section. That is, the bottom 351 of the recessed portions 35 is configured to have no undulations. Thus, when the guide wire 1A is operatively gripped, the skin 501 of the fingertip 500 reliably comes into contact with the bottom 351 of the protruding portion 35 so as to thereby more reliably prevent the grip force from lowering when the guide wire 1A is operated.

Preferably, the bottom 351 of the recessed portion 35 is roughened by, for example, surface roughening. That is, the bottom 351 of the recessed portion 35 is formed to have a number of minute asperities. This further increases the friction coefficient of each of the bottoms 351 of the recessed portions 35. Therefore, the sliding resistance between the bottoms 351 of the recessed portions 35 and the skin 501 of the fingertip 500 is increased when the guide wire 1A is operatively gripped. Thus, the fingertip 500 is reliably prevented from slipping relative to the guide wire 1A, whereby the pushability and torque at the hand portion is reliably transmitted to the distal end of the guide wire 1A.

As illustrated in FIG. 1, the protruding portion 34 is comprised of a high-density part 342 and a low-density part 343.

The high-density part 342 and the low-density part 343 are formed different from each other in terms of the arrangement or density of the linear member. That is, the interval (pitch) between the adjacent linear members 9A differs between the high-density part 342 and the low-density part 343. Stated differently, the density per unit area of the protruding portions in the high-density part 342 is greater than in the low-density part 343.

The high-density part 342 is a part of the protruding portion 34 having a higher arrangement density than that of the low-density part 343. The high-density part 342 extends from the middle portion or intermediate portion of the small diameter section 33 of the second wire 3 via the tapered section 32 to the middle portion or intermediate portion of the large diameter section 31. In the illustrated embodiment, the distal end of the high-density part 342 is located in the middle of the small diameter section 33 of the second wire 3 and the proximal end of the high-density part 342 is located in the middle of the large diameter section 31.

The low-density part 343 is located on the distal end side of the high-density part 342. The low-density part 343 extends from the middle portion or intermediate portion of the large diameter section 31 to the distal end portion of the large diameter section 31. In the illustrated embodiment, the distal end of the low-density part 343 is positioned in the middle of the large diameter section 31.

Since the high-density part 342 and the low-density part 343 are configured as described above, the portion of the guide wire 1A mainly inserted into the catheter 200 in the inserted state is such that a relatively high number of the tops 341 of the protruding portions 34 in the high-density part 342 can (positively) be brought into abutment against and slid along the inner wall 202 of the catheter 200. This can exhibit more satisfactory sliding performance. In addition, the gripped portion of the guide wire 1A is such that the bottoms 351 of the recessed portions 35 in the area of the low-density part 343 can be brought into more preferential abutment against the fingertip 500 than the tops 341 of the protruding portions 34 in the low-density part 343. Thus, the grip force can be more reliably inhibited or prevented from lowering when the guide wire 1A is operated.

As illustrated in FIG. 1, in the guide wire 1A, the occupancy of the protruding portions 34 on the external surface of the low-density part 343 is smaller than that of the recessed portions 35. This provides an advantage that when the guide wire 1A is successively inserted from its distal end side (the distal end 41), even if any portion of the external surface of the second wire 3 is gripped, it is possible to achieve a given or more grip force.

The protruding portion 34, i.e., the linear member 9A can be formed, for example, as described below.

First, a masking tape is spirally wound around the core 30 formed with the inner layer 7 and with the outer layer 8. The masking tape is spirally wound in those portions of the outer layer 8 excluding an area to be formed with the linear member 9A.

Next, the liquid resin material (hereinafter referred to as "the liquid material") to which is added the pigment is coated on (applied to) the exposed portion of the outer layer 8 where the masking tape is not wound. Examples of the coating method include a spray-used method and a dipping method. Next, the coated liquid material is dried. Thereafter, the masking tape is peeled off (removed). The linear member 9A can be formed by such steps.

The linear member 9A is uniform in width along its forming direction in the configuration illustrated in FIG. 1. However, the invention is not limited in this regard. For example, the linear member 9A may be varied in width along its forming direction. The width of the linear member 9A is preferably 0.1 to 1.2 mm, more preferably 0.3 to 0.9 mm. The axial length (i.e., the length in the wire-longitudinal direction) of the recessed portion 35 is preferably 0.3 to 1.8 mm, more preferably 0.5 to 1.5 mm. The height of the linear member 9A is preferably 5 to 15 μm, more preferably 7 to 13 μm. With the construction of the guide wire described above, the spaced apart protruding portions 34 and interposed recessed portions 35 form an undulating outer surface in the overall guide wire.

As illustrated in FIGS. 1 and 4, a covering layer 11 is provided at the distal end portion of the second wire 3 (i.e., an intermediate portion of the guide wire 1A), particularly at a portion located on the outer circumference of the tapered section 32. The covering layer 11 covers a distal end side portion (the distal end portion) of the high-density part 342 of the protruding portions 34. In this way, the linear member 9A and the outer layer 8 in the high-density part 342 are covered by the covering layer 11. This can reduce friction with the inner wall 202 of the catheter 200, which facilitates insertion. Further, the friction with the inner wall 202 of the catheter 200 can reliably inhibit or prevent the linear member 9A and the outer layer 8 from peeling off. Thus, the covering layer 11 functions as a protection layer for protecting the linear member 9A and the outer layer 8. Though the guide wire can be provided with a covering layer as described below, the covering layer does not fill the recessed portions 35. Thus, even with the covering layer 11 present, the spaced apart protruding portions 34 and interposed recessed portions 35 form the undulating outer surface in the overall guide wire and, in a longitudinal cross-section, the outer diameter of the guide wire in the recessed portions 35 is less than the outer diameter of the guide wire at the protruding portions 34.

Although not particularly restrictive, examples of the constituent material of the covering layer 11 include the fluorinated resin material discussed above in the explanation of the inner layer 7.

In the portion of the guide wire formed with the covering layer 11, the top 341 of the protruding portion 341 and the bottom 351 of the recessed portion 35 have the same friction coefficient.

Figure 5:
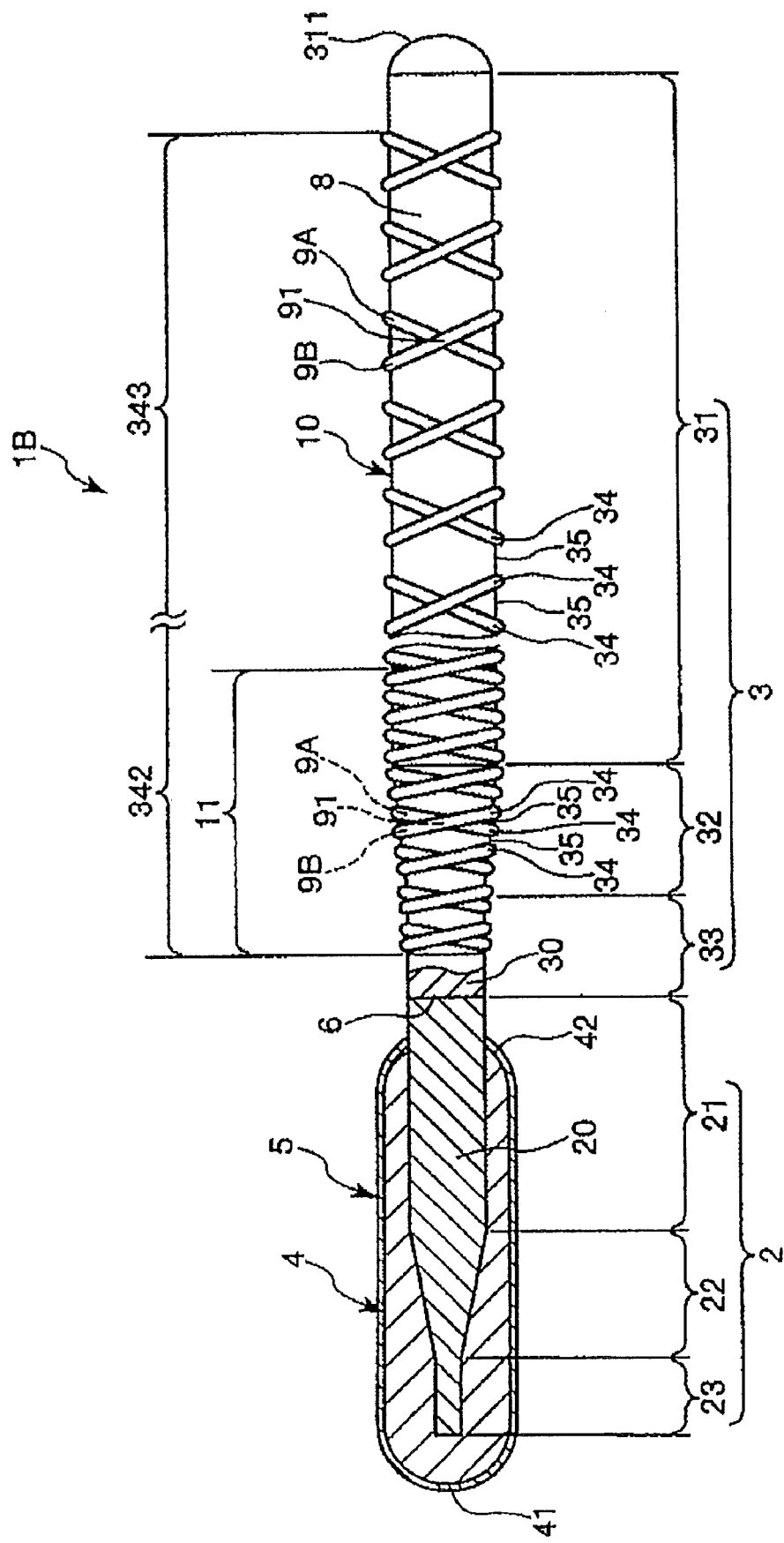
FIG. 5 is a partial longitudinal cross-sectional view illustrating a second embodiment of the guide wire disclosed here.

FIG. 5 is a partial longitudinal cross-sectional view illustrating a second embodiment of the guide wire disclosed here. The description of the second embodiment of the guide wire focuses primarily on aspects of the guide wire that differ from those associated with the embodiment described above. Features in the second embodiment of the guide wire that are the same as those in the earlier embodiment are identified by common reference numerals and a detailed description of such features is not repeated.

The second embodiment of the guide wire is the same as the first embodiment, except the configuration/shape of the protruding portion.

In addition to the first linear member 9A, the guide wire 1B illustrated in FIG. 5 includes another linear member (a second linear portion) 9B extending (spirally wound) in a direction opposite to the spiral winding direction of the first linear member 9A. The second linear member 9B is made of the same material as that of the first linear member 9A.

With such a configuration, the second wire 3 possesses a plurality of radially outwardly protruding portions 34 composed of the first linear members 9A and the second linear members 9B on the external surface thereof, and a recessed portion 35 formed between the adjacent protruding portions 34. Therefore, similar to the first embodiment, in the inserted state, a portion of the guide wire 1B that is inserted into the lumen 201 of the catheter 200 is configured as discussed below. The tops 341 of the protruding portions 34 each having a relatively low friction coefficient mainly come into abutment against the inner wall 202 of the catheter 200. In addition, the bottoms 351 of the recessed portions 35 each having a relatively high friction coefficient are prevented from coming into abutment against the inner wall 202 of the catheter 200. Thus, when the guide wire 1B is operated, the tops 341 of the protruding portions 34 slide along the inner wall 202 of the catheter 200, exhibiting satisfactory sliding performance. In addition, at the hand gripping portion, the fingertip 500 enters the recessed portion 35. Specifically, the skin 501 of the fingertip 500 mainly comes into abutment against the bottom 351 of the recessed portion 35 having a relatively high friction coefficient. Thus, a grip force can reliably be inhibited or prevented from being lowered when the guide wire 1B is operated.

In addition, the guide wire 1B (the second wire 3) is formed with intersecting portions 91 where the linear members 9A and the linear members 9B intersect each other. The fingertips 500 (the skin 501) gripping the guide wire 1B are tucked (seized) on the circumference (periphery) of the intersecting portion 91. Thus, the grip force can be reliably prevented from being lowered when the guide wire 1B is operated.

The linear member 9A and the linear member 9B may be the same or different from each other in friction coefficient. Examples of a method of making the linear member 9A and the linear member 9B different in friction coefficient from each other include changing the kind of the resin material forming the linear members 9A, 9B, and changing the content (amount) of pigment.

The number of second linear members 9B is preferably the same as that of the number of first linear members 9A. That is, in this illustrated embodiment, the first and second linear members 9A, 9B are each comprised of a single linear member, though each could be comprised of several linear member portions. However, the present invention is not limited to this. Indeed, the number of second linear members 9B may be different from the number of first linear members 9A.

Figure 6:
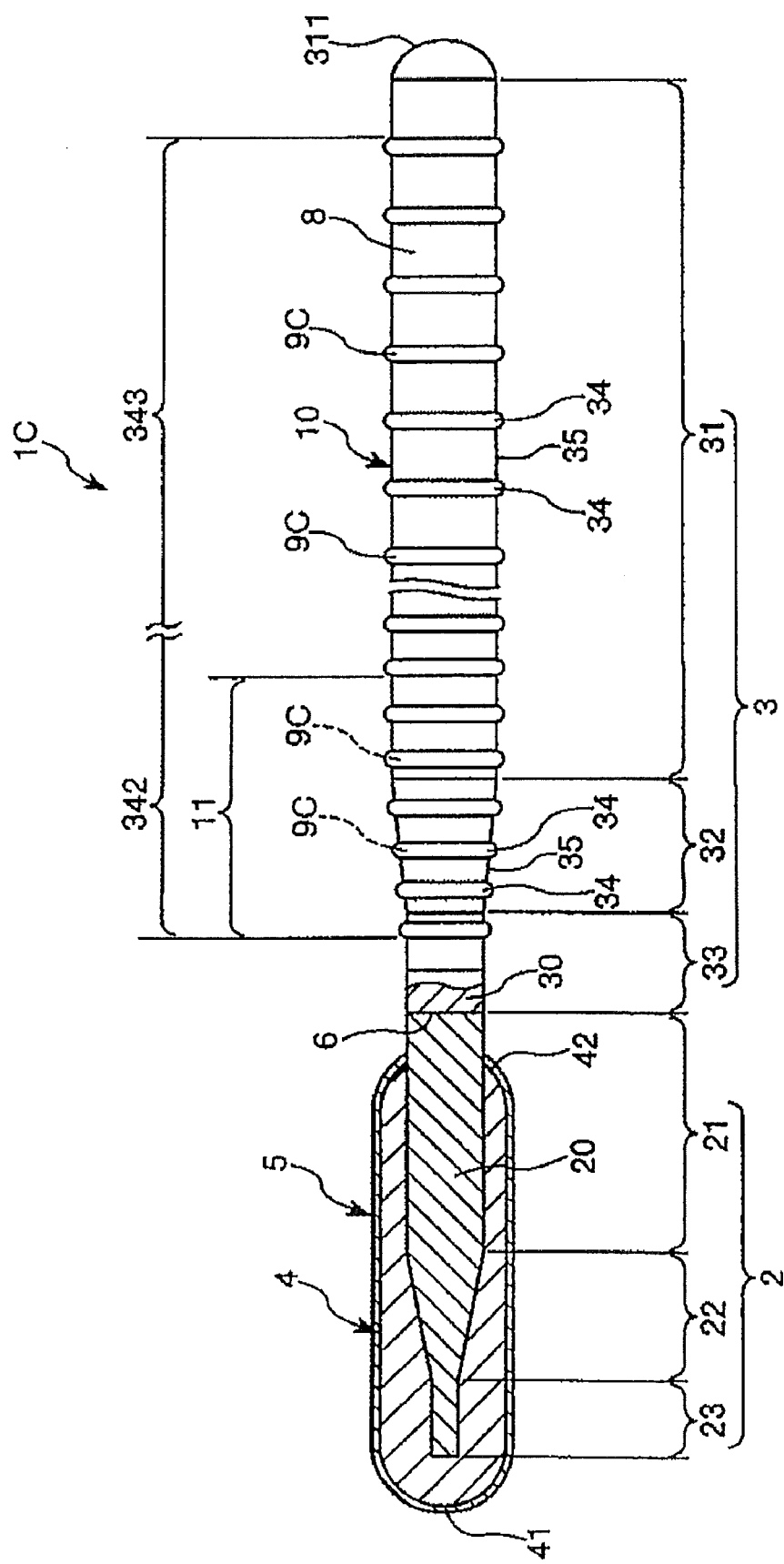
FIG. 6 is a partial longitudinal cross-sectional view illustrating a third embodiment of the guide wire disclosed here.

FIG. 6 illustrates a third embodiment of the guide wire disclosed here. The description of the third embodiment of the guide wire focuses primarily on aspects of the guide wire that differ from those associated with the embodiments described above. Features in the third embodiment of the guide wire that are the same as those in the earlier embodiment are identified by common reference numerals and a detailed description of such features is not repeated.

The third embodiment of the guide wire is the same as the first embodiment, except for the configuration of the protruding portion.

A guide wire 1C illustrated in FIG. 6 is such that the second wire 3 is formed with a plurality of ring-shaped or annular portions (linear members) 9C each configured to extend in the circumferential direction thereof. The ring-shaped portions 9C are each made of the same material as that of the linear member 9A.

These ring-shaped portions 9C are spaced apart from each other in the wire-longitudinal direction. With this, the second wire 3 has a plurality of radially outwardly protruding portions 34 formed of the ring-shaped portions 9C and recessed portions 35 each located between adjacent protruding portions 34 on the external surface of the layer 8. Thus, similar to the first embodiment, when the guide wire 1C is operated in the inserted state, the tops 341 of the protruding portions 34 slide along the inner wall 202 of the catheter 200, thereby exhibiting satisfactory sliding performance. At the hand portion, the skin 501 of the fingertip 500 comes into abutment against the bottom 351 of the recessed portion 35. This can reliably inhibit or prevent the grip force from lowering when the guide wire 1C is operated.

Figure 7:
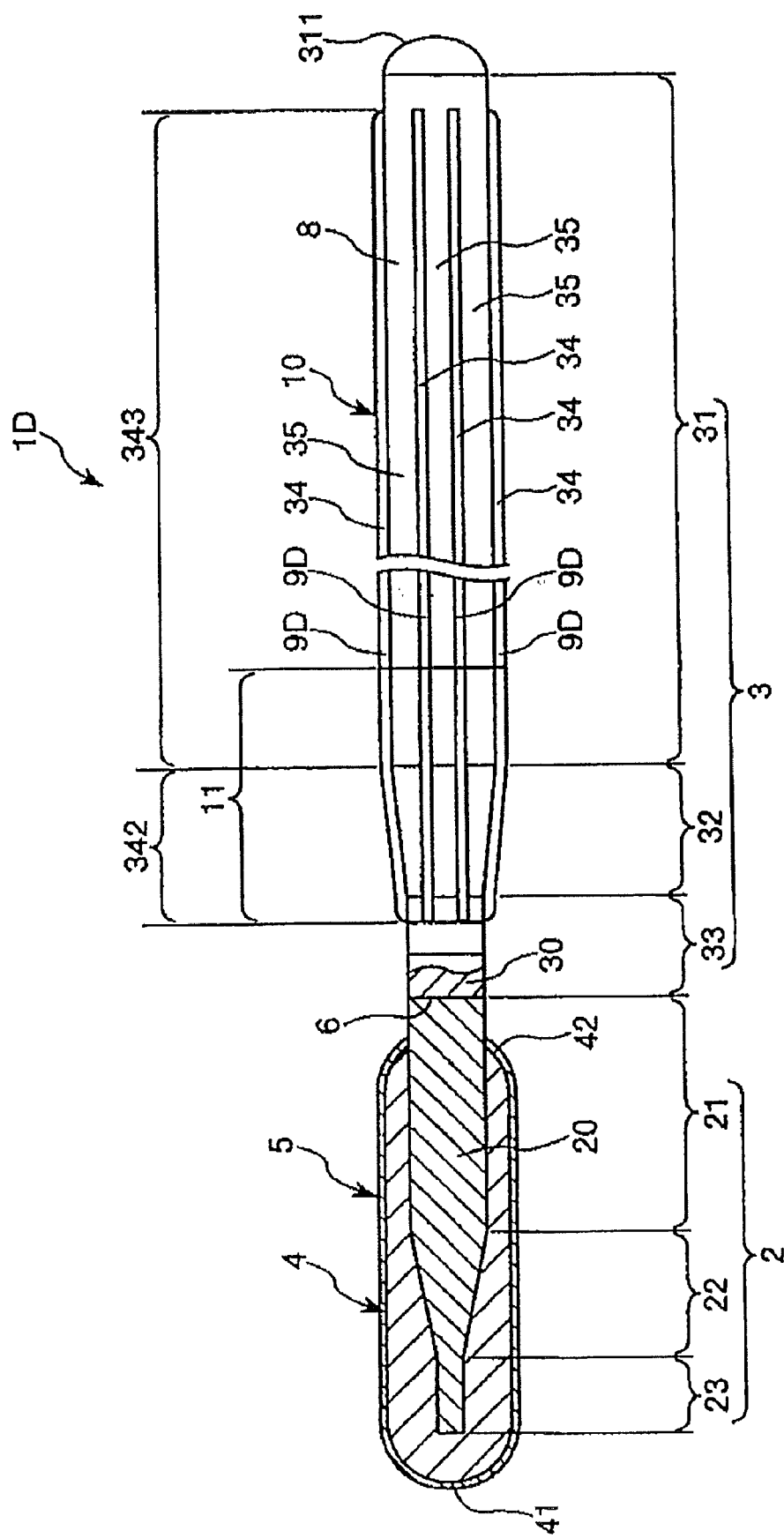
FIG. 7 is a partial longitudinal cross-sectional view illustrating a fourth embodiment of the guide wire disclosed here.

FIG. 7 is a partial cross-sectional longitudinal view illustrating a fourth embodiment of the guide wire disclosed here. The description of the fourth embodiment of the guide wire focuses primarily on aspects of the guide wire that differ from those associated with the embodiments described above. Features in the fourth embodiment of the guide wire that are the same as those in the earlier embodiments are identified by common reference numerals and a detailed description of such features is not repeated.

The fourth embodiment is the same as the first embodiment, except for the configuration of the protruding portion.

A guide wire 1D illustrated in FIG. 7 is configured so that the second wire 3 includes a plurality of linear members 9D (six in the present embodiment) extending linearly and axially along its longitudinal direction (parallel to the central axis of the wire body). The linear members 9D each extend (span) from the proximal end portion of the small diameter section 33 of the second wire 3 to the proximal end portion of the large diameter section 31 of the second wire 3. Also, the linear members 9D are made of the same material as that of the linear member 9A.

The linear members 9D are circumferentially arranged or spaced at equal intervals (at given intervals) on the outer circumference (external surface) of the second wire 3. With this, the second wire 3 has a plurality of axially extending radially outwardly protruding portions 34 formed of the linear members 9D on the outer surface and axially extending recessed portions 35 each formed between adjacent protruding portions 34. Thus, similar to the first embodiment, when the guide wire 1D is operated in the inserted state, the tops 341 of the protruding portions 34 slide along the inner wall 202 of the catheter 200, exhibiting satisfactory sliding performance. The respective protruding portions 34 are formed of the linear members 9D extending linearly in the wire-longitudinal direction. Therefore, when the guide wire 1D is shifted along the wire-longitudinal direction, its shifting direction is a direction where the protruding portions 34 are more easily slidable. Thus, the shifting operation of the guide wire 1D becomes easier. At the hand gripping portion, the skin 500 of the fingertip 500 abuts against the bottom 351 of the recessed portion 35, which can reliably inhibit or prevent the grip force from lowering when the guide wire 1D is operated.

The width of each linear member 9D is constant along the longitudinal direction of the second wire 3. However, the guide wire here is not limited in this regard. The width of each linear member 9D may be varied.

In addition, the height of each linear member 9D is constant along the longitudinal direction of the second wire 3. Once again, the guide wire here is not limited in this regard as the height of each linear member 9D may be varied.

The illustrated embodiment of the guide wire includes six linear members 9D. However, other numbers of linear members may be provided. The number of linear members 9D may be e.g., two, three, four, five, seven or more.

Figure 8:
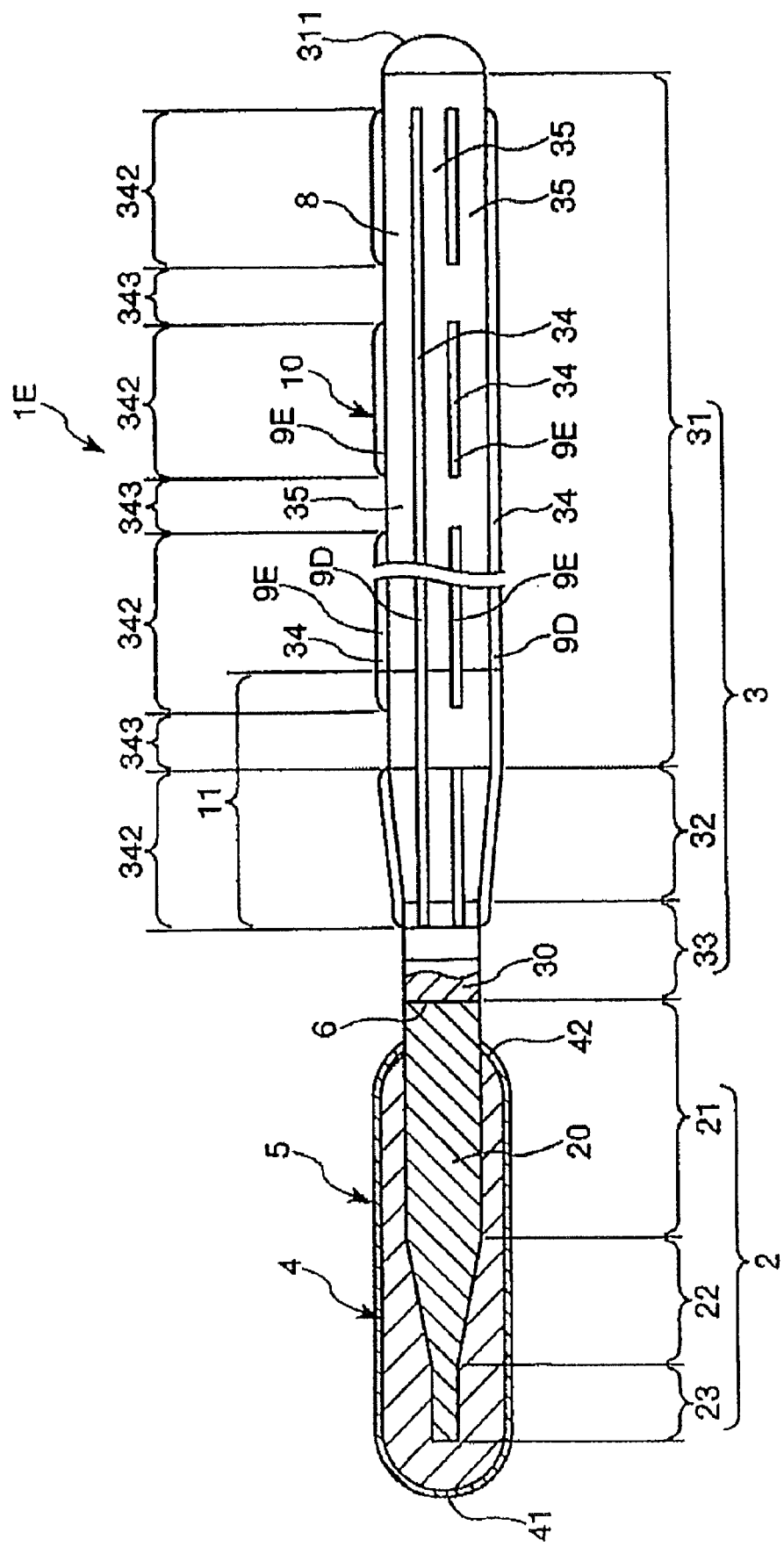
FIG. 8 is a partial longitudinal cross-sectional view illustrating a fifth embodiment of the guide wire disclosed here.

FIG. 8 is a partial longitudinal cross-sectional view of a fifth embodiment of the guide wire. The description of the fifth embodiment of the guide wire focuses primarily on aspects of the guide wire differing from those associated with the embodiments described above. Features in the fifth embodiment of the guide wire that are the same as those in the earlier embodiments are identified by common reference numerals and a detailed description of such features is not repeated.

The fifth embodiment disclosed here is the same as the fourth embodiment, except for differences in the configuration of the linear members.

A guide wire 1E illustrated in FIG. 8 is configured such that the second wire 3 is includes a plurality of axially extending linear members 9D (three in the present embodiment) of a relatively longer length and a plurality of axially extending linear members 9E each of a relatively shorter length than the relatively longer linear members 9D. The linear members 9E of relatively shorter length are positioned between the linear members 9D relatively longer length so that in the circumferential direction the relatively longer linear members 9D alternate with the relatively shorter linear members 9E. In addition, there are a plurality (four in the illustrated embodiment) of the shorter linear members 9E that are axially aligned (co-linear) with each other. Thus, in the circumferential direction, the second wire 3 includes a relatively longer linear member 9D, a set of four axially or longitudinally aligned shorter linear members 9E, another relatively longer linear member 9D, another set of four longitudinally aligned shorter linear members 9E, a further relatively longer linear member 9D, and a further set of four longitudinally aligned shorter linear members 9E, arranged in that order. The linear members 9D, 9E provide radially outwardly protruding portions.

The guide wire 1E configured as above includes a high-density part 342 where both the linear members 9D and the linear members 9E are circumferentially arranged, and a low-density part 343 where the linear members 9E are circumferentially omitted (absent) but the linear members 9D are arranged alternately in the wire-longitudinal direction. Thus, parts of the guide wire can be formed different from each other in sliding performance. With such a configuration, the configuration of the guide wire 1E is effective.

Figure 9:
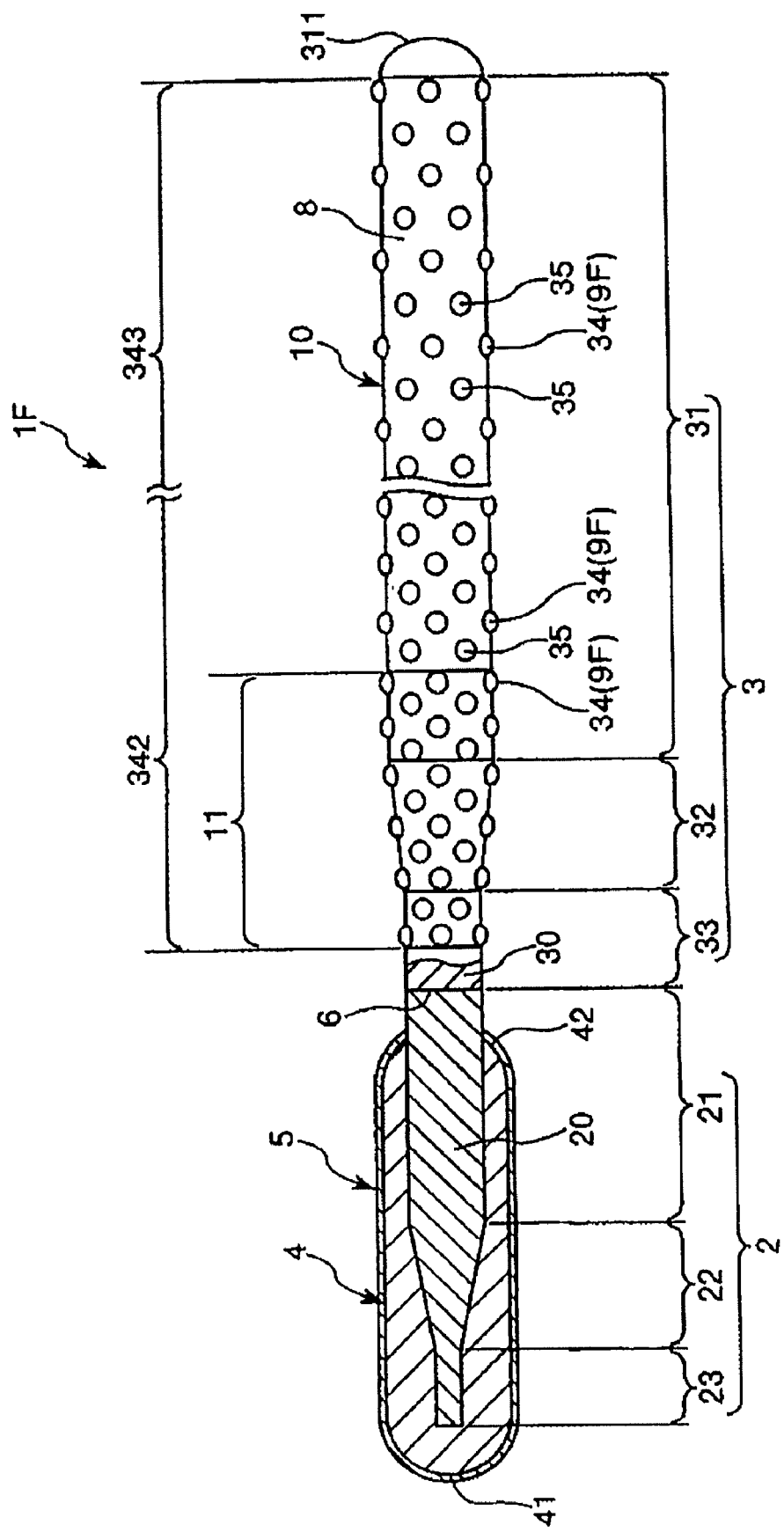
FIG. 9 is a partial longitudinal cross-sectional view illustrating a sixth embodiment of the guide wire disclosed here.

FIG. 9 is a partial longitudinal cross-sectional view illustrating a sixth embodiment of the guide wire disclosed here. The description of the sixth embodiment of the guide wire focuses primarily on aspects of the guide wire that differ from those associated with the embodiments described above. Features in the sixth embodiment of the guide wire that are the same as those in the earlier embodiment are identified by common reference numerals and a detailed description of such features is not repeated.

The sixth embodiment of the guide wire is the same as the first embodiment, except for the configuration of the protruding portions.

The guide wire 1F illustrated in FIG. 9 includes a number of dome-like dots 9F arranged in a scattered manner on the second wire 3. The second wire 3 thus comprises a plurality of radially outwardly protruding portions 34 formed of the dots 9F on the external surface and recessed portions 35 each formed between the adjacent protruding portions or dots 34. The dots 9F are each made of the same material as that of the linear member 9A.

As with the first embodiment, when the guide wire 1F is operated in the inserted state, the tops 341 of the respective protruding portions 34 slide along the inner wall 202 of the catheter 200, which exhibits satisfactory sliding performance. At the hand gripping portion, the skin 501 of the fingertip 500 abuts against the bottom 351 of the recessed portion 35, which can reliably prevent the grip force from being lowered when the guide wire 1F is operated.

The respective dots 9F have the same diameter in the illustrated embodiment. However, the guide wire here is not limited in this regard as the dots 9F may have different diameters.

In addition, the respective dots 9F have the same height, though the guide wire is not limited to this configuration. The dots 9F may have different heights.

Figure 10:
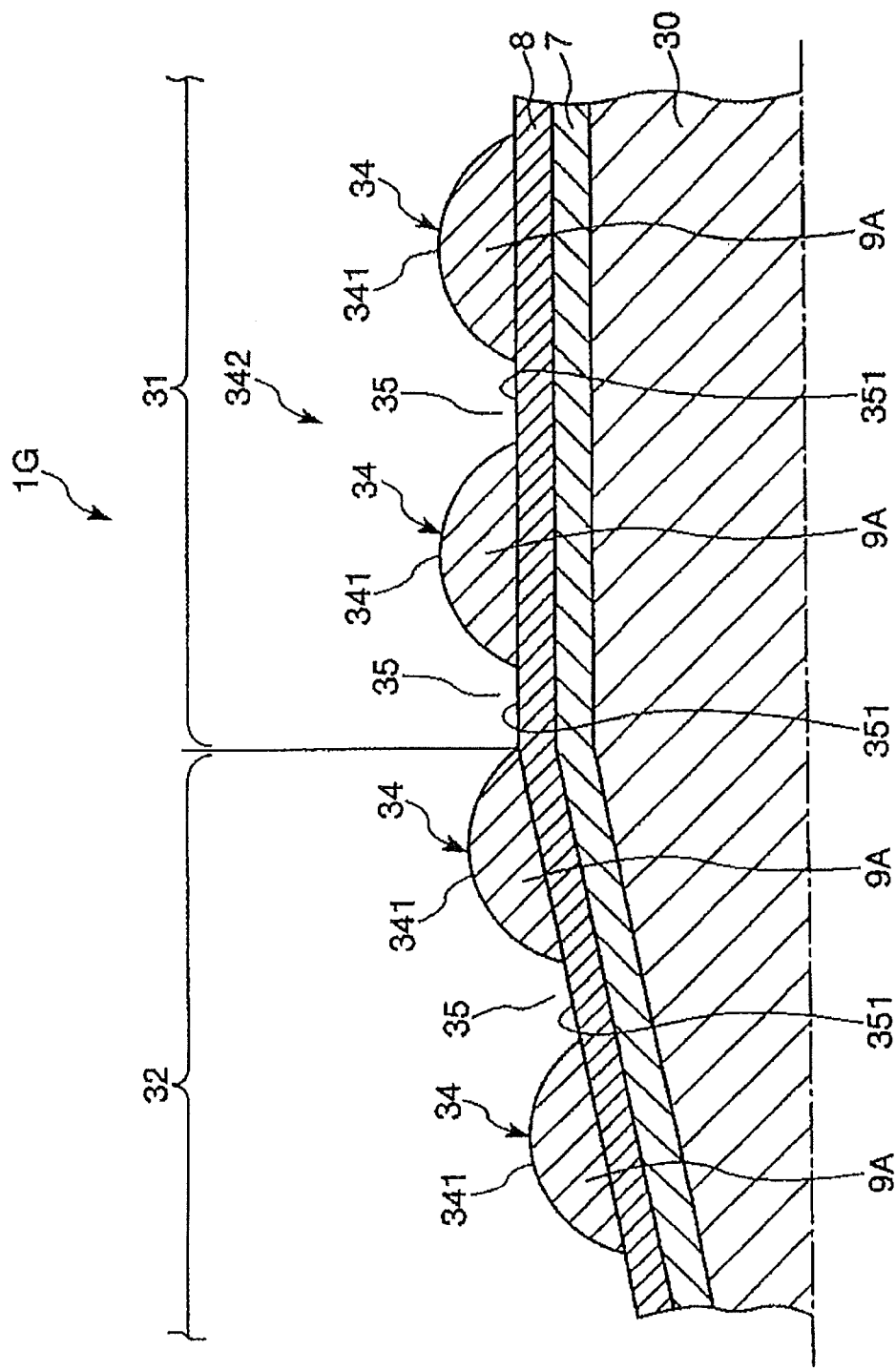
FIG. 10 is an enlarged longitudinal cross-sectional view illustrating a seventh embodiment of the guide wire disclosed here.
Figure 11:
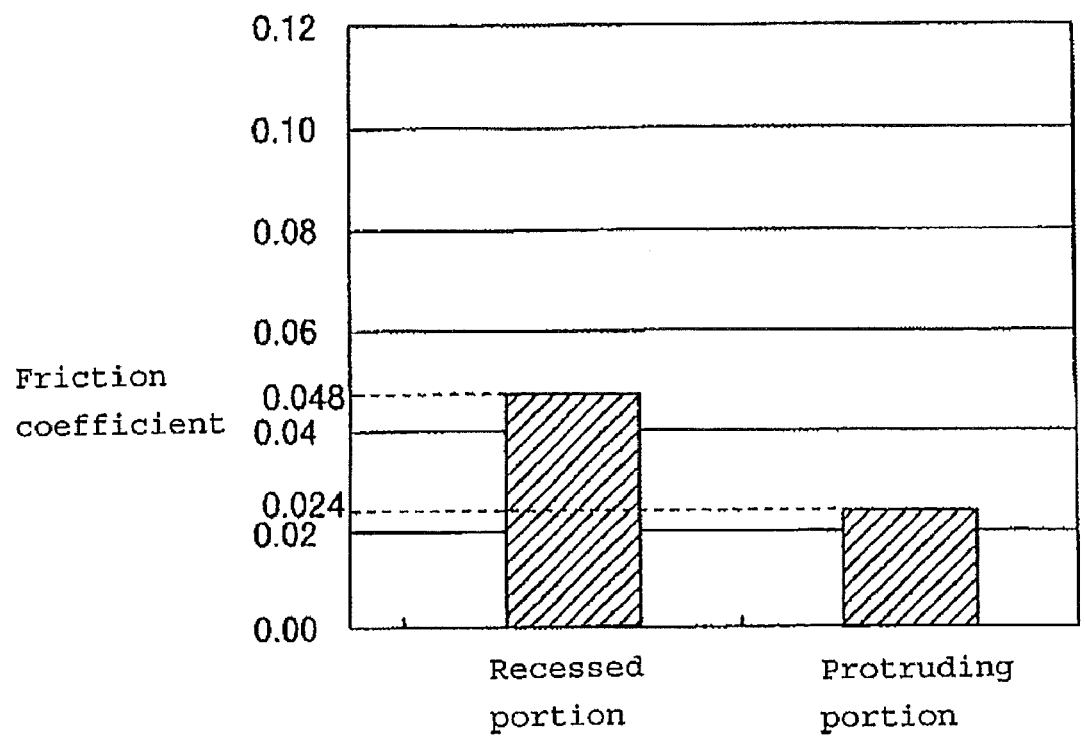
FIG. 11 is a graph showing respective friction coefficients of a recessed portion and a protruding portion of the guide wire illustrated in FIG. 1.

FIG. 10 is an enlarged longitudinal cross-sectional view illustrating a seventh embodiment of the guide wire disclosed here. The description of the seventh embodiment of the guide wire focuses primarily on aspects of the guide wire that differ from those associated with the embodiment described above. Features in the seventh embodiment of the guide wire that are the same as those in the earlier embodiment are identified by common reference numerals and a detailed description of such features is not repeated.

The seventh embodiment is the same as the first embodiment, except that the covering layer, which covers the distal end side portion of the high-density part of the protruding portion, is omitted.

As shown in FIG. 10, the guide wire 1G does not include the covering layer like the covering layer 11 in the first embodiment. With this construction, the linear members 9A and the outer layer 8 in the high-density part 342 are exposed. The high-density part 342 spans or extends from the tapered section 32 to the large diameter section 31 in the second wire 3. Indeed, in this embodiment shown in FIG. 10, the high-density part 342 begins and ends at the same places shown in FIG. 1. In particular, the vicinity of the border portion between the tapered section 32 and the large diameter section 31 is a part where the friction with the inner wall 202 of the catheter 200 relatively easily occurs when the guide wire 1G is operated in the inserted state. Since the high-density part 342 is located at this part, sliding performance can reliably be inhibited or prevented from being lowered when the guide wire 1G is operated, and the linear member 9A and the outer layer 8 can reliably be inhibited or prevented from being peeled off due otherwise to the friction.

Although the illustrated embodiments of the guide wire disclosed here are described as above, the invention is not limited to these. Portions of the guide wire can be replaced with other constituent parts capable of exhibiting the same function. In addition, parts or features can be added.

The guide wire disclosed here may be a combination of two or more configurations (features) in the respective or different embodiments.

The distal end member made of a resin material is arranged on the outer circumference of the distal end portion of the wire body so as to cover the distal end portion. However, the guide wire is not limited to this. For example, a coil made of a metal material may be disposed at the outer circumference of the distal end portion of the wire body. In all the embodiments described above, the spaced apart protruding portions 34 and interposed recessed portions 35 form an undulating outer surface in the overall guide wire. Though the guide wire can be provided with a covering layer as described, the covering layer does not fill in the recessed portions 35. Thus, the undulating outer surface of the guide wire is maintained even when the coating layer is applied. In a longitudinal cross-section of the finished guide wire, the outer diameter of the guide wire in the recessed portions 35 is less than the outer diameter of the guide wire at the protruding portions.

A description is next given of a working example disclosed here.

WORKING EXAMPLE 1

The guide wire illustrated in FIG. 1 was manufactured in which the core forming the wire body was made of a Ni—Ti alloy. The outer layer was made of PTFE, FEP, a binder resin and pigment and the linear member was made of PTFE and pigment. Unlike FIG. 1, the pitch of the linear member is constant along the wire-longitudinal direction.

COMPARATIVE EXAMPLE 1

Glidewire Advantage (manufactured by TERUMO CORPORATION) was used as a guide wire. The linear member as in the first embodiment was not provided on the external surface of this guide wire.

COMPARATIVE EXAMPLE 2

The guide wire similar to that in the first embodiment was used to manufacture a guide wire, except that a covering layer of polytetrafluoroethylene (PTFE) was provided on the outer surface substantially fully. Therefore the recessed portions of the Comparative Example 2 are covered by the PTFE layer.

<Torque Test>

Torque tests (torque tests 1 to 3) described above were performed on the respective guide wires of Working Example 1 and Comparative Examples 1 and 2.

Figure 12:
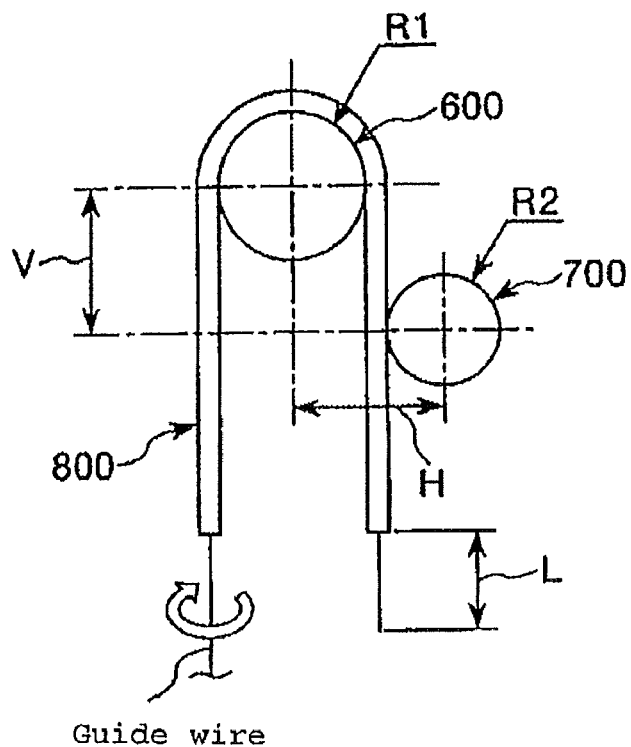
FIG. 12 is an explanatory view illustrating a state of a torque test.
Figure 13:
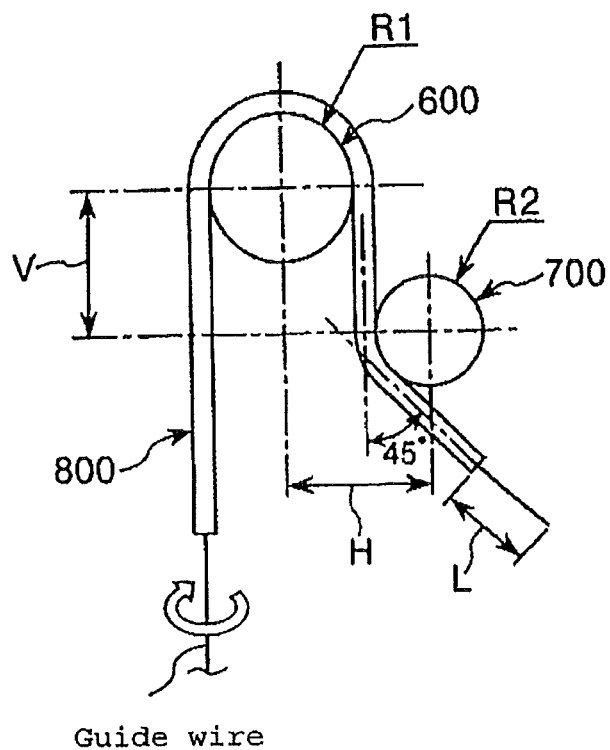
FIG. 13 is an explanatory view illustrating another state of a torque test.
Figure 14:
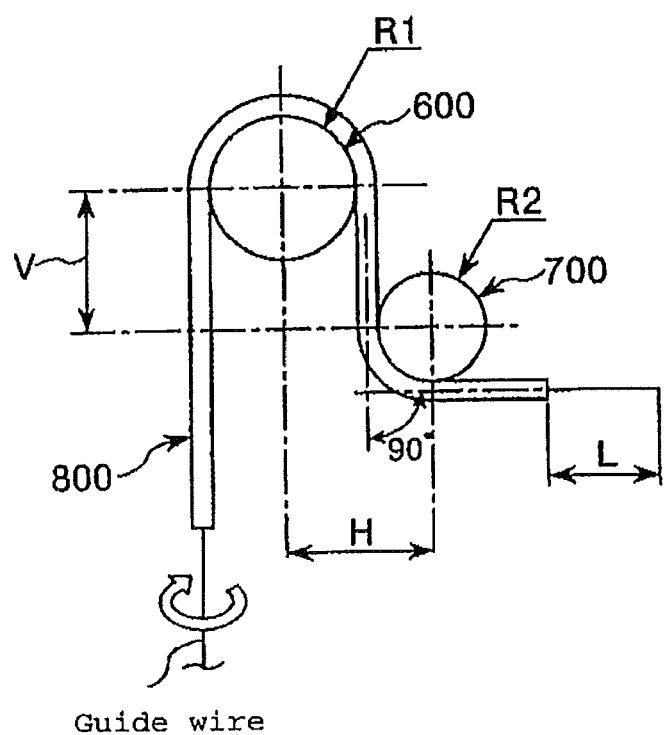
FIG. 14 is an explanatory view illustrating another state of a torque test.

Referring to FIGS. 12-14, torque tests 1 to 3 were performed using the test equipment mentioned below. This test equipment includes a first member 600 formed in a circular cylinder with radius R1 and a second member 700 formed in a circular cylinder with a radius R2 of 20 mm. In addition, these members were arranged and secured so as to have a vertical center-to-center distance of 50 to 70 mm and a horizontal center-to-center distance of 50 to 70 mm.

The first members 600 had respective radii R1 of 30 mm, 40 mm and 50 mm. These members were selectively used one by one.

(Torque Test 1)

Referring to FIG. 12, a catheter 800 (manufactured by TERUMO CORPORATION: Radifocus Catheter M) of 5 Fr. (French) was prepared, wound around the first member 600, and installed such that both the ends thereof vertically face downwards.

Next, a single guide wire was inserted into the catheter 800 so that opposite ends projected from respective opposite ends of the catheter 800. A projecting amount L of the guide wire on the distal end side (on the side of the second member 700) was 40 mm.

Next, in this state, the guide wire was gripped at its proximal end portion and operatively turned around the central axis of the guide wire in one direction. In this way, the easiness of turning operation was evaluated.

The evaluation results are shown in Table 1 below. In Table 1, A denotes "easy to turn," B "able to turn," C "hard to turn" and D "not able to turn". (These apply to torque tests 2 and 3.)

(Torque Test 2)

Referring to FIG. 13, a catheter 800 was prepared, allowed to extend around the first member 600 and around the second member 700, and installed such that the second member 700 allows the central axes of portions of the catheter on the distal end side and the proximal end side of the second member 700 to form an angle of 45° therebetween.

Next, a single guide wire was inserted into the catheter 800 so that opposite ends of the guide wire projected from respective opposite ends of the catheter 800. A projecting amount L of the guide wire on the distal end side (on the side of the second member 700) was 40 mm.

Next, in this state, the guide wire was gripped at its proximal end portion and operatively turned around the guide wire central axis in one direction. In this way, the easiness of the turning operation was evaluated. The evaluation results are shown in Table 1.

(Torque Test 3)

Referring to FIG. 14, a catheter 800 was prepared, allowed to extend around the first member 600 and around the second member 700, and installed such that the second member 700 causes the central axes of portions of the catheter on the distal end side and the proximal end side of then second member 700 to form an angle of 90° therebetween.

Next, a single guide wire was inserted into the catheter 800 so that opposite ends of the guide wire projected from respective opposite ends of the catheter 800. A projecting amount L of the guide wire on the distal end side (on the side of the second member 700) was 40 mm.

Next, in this state, the guide wire was gripped at its proximal end portion and operatively turned around the guide wire central axis in one direction. In this way, the easiness of turning operation was evaluated.

The evaluation results are shown in Table 1.

TABLE 1

| | Torque test 1 | | | Torque test 2 | | | Torque test 3 | | |
|---|---|---|---|---|---|---|---|---|---|
| | R1 = 30 [mm] | R1 = 40 [mm] | R1 = 50 [mm] | R1 = 30 [mm] | R1 = 40 [mm] | R1 = 50 [mm] | R1 = 30 [mm] | R1 = 40 [mm] | R1 = 50 [mm] |
| Working Example 1 | A | A | A | A | A | A | A | A | A |
| Comparative Example 1 | A | A | A | A | A | A | B | A | A |
| Comparative Example 2 | C | C | C | C | C | C | D | C | C |

As clear from Table 1, all the torque tests produced results for the guide wire of Working Example 1 that are "easy to operatively turn," that is "excellent in operability". This means that the guide wires according to Working Example 1 are excellent in sliding performance with respect to the catheter 800 and the grip force is reliably inhibited or prevented from being lowered when the guide wire is gripped and operated.

On the other hand, results were obtained that the guide wires of Comparative Examples 1 and 2 are "poor in operability" or "poor in operability according to the conditions of the torque test in some cases".

The guide wires illustrated in FIGS. 5-10 were manufactured and subjected to the same tests. Consequently, almost the same evaluation results as those of the Working Example 1 were obtained by the respective guide wires.

It should be understood by those skilled in the art that various modifications, combinations, sub-combinations and alterations may occur depending on design requirements and other factors insofar as they are within the scope of the appended claims or equivalents thereof. Thus, the detailed description above describes preferred embodiments of the guide wire disclosed, but it is to be understood that the invention is not limited to those precise embodiments described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A guide wire comprising:
an elongated flexible wire body possessing an outer diameter and an external surface;
the elongated flexible wire body comprising a distal end portion and a proximal end portion;
the elongated flexible wire body comprising a first constant diameter section at which the outer diameter of the elongated flexible wire body is a constant outer diameter;
the elongated flexible wire body comprising a second constant diameter section at which the outer diameter of the elongated flexible wire body is a constant outer diameter less than the constant outer diameter of the first constant diameter section;
the elongated flexible wire body comprising a tapered section at which the outer diameter of the elongated flexible wire body varies from the constant outer diameter of the first constant diameter section to the constant outer diameter of the second constant diameter section;
the tapered section being positioned axially between the first constant diameter section and the second constant diameter section;
the first constant diameter section being positioned proximally of the second constant diameter section;
the wire body comprising a plurality of radially outward protruding portions spaced apart from one another;
the protruding portions extending further radially outwardly than portions of the outer surface of the flexible wire body surrounding the protruding portions so that recessed portions exist between adjacent protruding portions;
the guide wire possessing an undulating outermost surface by virtue of the protruding portions and the recessed portions;
the protruding portions being located in the first constant diameter section, the tapered section, and the second constant diameter section;
the protruding portions having an outermost surface made of a material possessing a first dynamic friction coefficient, the recessed portions having an outermost surface made of a material possessing a second dynamic friction coefficient, wherein the first dynamic friction coefficient is smaller than the second dynamic friction coefficient;
wherein the wire body comprises a core and an outer layer overlying the core, the protruding portions overlying the outer layer, the outer layer possessing an exposed surface which is the outermost surface of the recessed portions; and
wherein the outer layer is made of a fluorinated resin material and pigment, the protruding portions are made of a fluorinated resin material and pigment, and a content rate of pigment in the protruding portions is smaller than a content rate of pigment in the outer layer.

2. The guide wire according to claim 1, wherein the protruding portions in a first circumferential portion of the flexible wire body are arranged so that a density of the protruding portions per unit area is greater than in a second circumferential portion of the flexible wire body, the first portion being located distally of the second portion.

3. The guide wire according to claim 2, wherein the protruding portions are comprised of a spirally extending linear member.

4. The guide wire according to claim 3, wherein a spacing between axially adjacent windings of the spirally extending linear member in the first circumferential portion is less than the spacing between axially adjacent windings of the spirally extending linear member in the second circumferential portion.

5. The guide wire according to claim 2, wherein the protruding portions are comprised of a spirally extending first linear member, wherein a spacing between axially adjacent windings of the spirally extending first linear member in the first circumferential portion is less than the spacing between axially adjacent windings of the spirally extending first linear member in the second circumferential portion, and further comprising a spirally extending second linear member separate from the first spirally extending linear member, the spirally extending first and second linear members being wound in opposite direction.

6. The guide wire according to claim 1, wherein the protruding portions are spaced apart dots possessing a semicircular shape.

7. The guide wire according to claim 1, wherein the protruding portions are longitudinally extending linear members extending parallel to a central axis of the wire body, adjacent ones of the linear members being spaced apart from each other in a circumferential direction, each of the linear members having a distal end and a proximal end, each linear member extending in an uninterrupted manner from its distal end to its proximal end, the distal end of each linear member being located in the first constant diameter section and the proximal end of each linear member being located in the second constant diameter section.

8. The guide wire according to claim 1, wherein the protruding portions are longitudinally extending linear members extending parallel to a central axis of the wire body, the linear members comprising first and second linear members that are circumferentially spaced apart from one another, the first and second linear members each having a distal end located in the first constant diameter section and a proximal end being located in the first constant diameter section, the first and second linear members each extending in an uninterrupted manner from its distal end to its proximal end, the linear members also comprising a plurality of coaxially arranged third linear members positioned between the first and second linear members, the third linear members being separate from one another and axially spaced apart from each other, the linear members also comprising a plurality of coaxially arranged fourth linear members positioned between the first and second linear members, the fourth linear members being separate from one another and axially spaced apart from each other, the third linear members being circumferentially spaced apart from one another.

9. The guide wire according to claim 1, wherein the protruding portions are comprised of a plurality of axially spaced apart and separate ring-shaped members each extending in a circumferential direction.

10. The guide wire according to claim 1, wherein the outermost surface of the protruding portions is rounded.

11. A guide wire comprising:
a wire comprising a flexible elongate wire body possessing an exposed external surface;
the wire body comprising a protruding portion positioned on the external surface and a non-protruding portion positioned adjacent the protruding portion, the protruding portion possessing an exposed outer surface;

the exposed outer surface of the protruding portion is comprised of a material possessing a dynamic friction coefficient smaller than the dynamic friction coefficient of a material forming the exposed external surface of the non-protruding portion so that the dynamic friction coefficient of the exposed outer surface of the protruding portion is smaller than the dynamic friction coefficient of the exposed external surface of the wire body at the non-protruding portion; and wherein the non-protruding portion is made of a fluorinated resin material and pigment, the protruding portion is made of a fluorinated resin material and pigment, and a content rate of pigment in the protruding portion is smaller than a content rate of pigment in the non-protruding portion.

12. The guide wire according to claim 11, wherein a top of the protruding portion possess an outermost surface that is rounded.

13. The guide wire according to claim 11, wherein the outer surface of the flexible wire body in the non-protruding portion extends linearly along a longitudinal direction of the wire body as viewed in longitudinal cross-section.

14. The guide wire according to claim 11, wherein the wire body has a distal portion, an intermediate portion and a proximal portion, the exposed external surface of the wire body at the non-protruding portion on the intermediate portion and the exposed outer surface of the protruding portion on the intermediate portion has the same friction coefficient, and the friction coefficient of the exposed outer surface of the protruding portion on the proximal portion is smaller than the exposed external surface of the wire body at the non-protruding portion on the proximal portion.

15. The guide wire according to claim 11, wherein the protruding portion in a first circumferential portion of the flexible wire body are arranged so that a density of the protruding portion per unit area is greater than in a second circumferential portion of the flexible wire body, the first portion being located distally of the second portion.

16. The guide wire according to claim 11, wherein the protruding portion is comprised of a spirally extending linear member.

17. The guide wire according to claim 11, wherein the protruding portion is spaced apart dots possessing a semi-circular shape.

18. The guide wire according to claim 11, wherein the protruding portion are longitudinally extending linear members extending parallel to a central axis of the wire body, adjacent ones of the linear members being spaced apart from each other in a circumferential direction, each of the linear members having a distal end and a proximal end, each linear member extending in an uninterrupted manner from its distal end to its proximal end.

19. A guide wire comprising:

an elongated flexible wire body;

the wire body comprising a plurality of radially outward protruding portions spaced apart from one another, wherein recessed portions exist between adjacent protruding portions;

the guide wire possessing an undulating outermost surface by virtue of the protruding portions and the recessed portions;

the protruding portions having an outermost surface made of a material possessing a first dynamic friction coefficient, the recessed portions having an outermost surface made of a material possessing a second dynamic friction coefficient, wherein the first dynamic friction coefficient is smaller than the second dynamic friction coefficient; and wherein the recessed portions are made of a fluorinated resin material and pigment, the protruding portions are made of a fluorinated resin material and pigment, and a content rate of pigment in the protruding portions is smaller than a content rate of pigment in the recessed portions.

20. The guide wire according to claim 19, wherein the protruding portions terminate in a distal direction of the guide wire at a termination point, and further comprising a distal end member covering at least a part of the distal end portion of the wire body including a distal-most end of the wire body, the distal end member being made of a flexible material, the distal end member possessing a proximal-most end which is distally spaced from the termination point.

21. The guide wire according to claim 19, wherein the protruding portions terminate in a distal direction of the guide wire at a termination point and wherein the wire body is comprised of a first wire possessing a proximal end and a second wire possessing a distal end, the first wire being positioned distally of the second wire, the proximal end of the first wire being connected to the distal end of the second wire at a joint, the termination point being located proximally of the joint.

22. The guide wire according to claim 21, wherein the first wire and the second wire are made of different materials.

23. The guide wire according to claim 1, wherein the protruding portions are semi-circular in shape taken along a longitudinal cross-section of the guide wire.

24. The guide wire according to claim 11, wherein the protruding portion is semi-circular in shape taken along a longitudinal cross-section of the guide wire.

25. The guide wire according to claim 19, wherein the protruding portions are semi-circular in shape taken along a longitudinal cross-section of the guide wire.

* * * * *